(12) United States Patent
Weinberg

(10) Patent No.: US 7,655,242 B2
(45) Date of Patent: Feb. 2, 2010

(54) DEFENSIN-INDUCING AGENTS

(75) Inventor: Aaron Weinberg, Shaker Heights, OH (US)

(73) Assignee: Case Western Reserve University, Cleveland, OH (US)

( * ) Notice: Subject to any disclaimer, the term of this patent is extended or adjusted under 35 U.S.C. 154(b) by 382 days.

(21) Appl. No.: 10/538,811

(22) PCT Filed: Dec. 15, 2003

(86) PCT No.: PCT/US03/40221

§ 371 (c)(1), (2), (4) Date: Mar. 9, 2006

(87) PCT Pub. No.: WO2004/055041

PCT Pub. Date: Jul. 1, 2004

(65) Prior Publication Data

US 2007/0117741 A1    May 24, 2007

Related U.S. Application Data

(60) Provisional application No. 60/433,100, filed on Dec. 13, 2002.

(51) Int. Cl.
*A61K 39/02* (2006.01)
*A61K 45/00* (2006.01)
*A61K 39/00* (2006.01)

(52) U.S. Cl. .............. 424/234.1; 424/278.1; 424/185.1; 424/192.1

(58) Field of Classification Search .............. 424/234.1, 424/278.1
See application file for complete search history.

(56) References Cited

U.S. PATENT DOCUMENTS 6,809,181 B2    10/2004    McCray et al.

FOREIGN PATENT DOCUMENTS

| JP | 2002186485 | 7/2002 |
|---|---|---|
| WO | 99/64439 | 12/1999 |
| WO | 01/38349 | 5/2001 |
| WO | 02/22686 | 3/2002 |
| WO | 02/064154 | 8/2002 |

OTHER PUBLICATIONS

Krisanaprakornkit et al. (Infection and Immunity, 2000; 68(5): 2907-2915).*
Seffernick et al (J. Bacteriology, 2001; 183: 2405-2410).*
Bowie et al. (Science, 1990, 257:1306-1310).*

* cited by examiner

*Primary Examiner*—Robert B Mondesi
*Assistant Examiner*—Lakia J Tongue
(74) *Attorney, Agent, or Firm*—John J. Cunniff; Hahn Loeser & Parks LLP

(57) ABSTRACT

This application provides, in part, novel polypeptides and nucleic acids that affect induction of defensins, and methods of making and using same.

11 Claims, 12 Drawing Sheets

A.

B.

hBD-2

HK5 hBD-2

IL-8

HK5

SEQUENCE LISTING

```
<160> NUMBER OF SEQ ID NOS: 8

<210> SEQ ID NO 1
<211> LENGTH: 121
<212> TYPE: PRT
<213> ORGANISM: Fusobacterium nucleatum

<400> SEQUENCE: 1

Met Ser Leu Phe Leu Val Ala Cys Gly Glu Lys Lys Glu Glu Glu Lys
1               5                   10                  15

Pro Ala Glu Gln Ala Ala Val Glu Ala Thr Ala Thr Glu Ala Pro Ala
            20                  25                  30

Thr Glu Thr Thr Glu Ala Ala Ala Glu Ala Lys Thr Phe Ser Leu Lys
        35                  40                  45

Thr Glu Asp Gly Lys Glu Phe Thr Leu Val Val Ala Ala Asp Gly Ser
    50                  55                  60

Thr Ala Thr Leu Thr Asp Ala Glu Gly Lys Ala Thr Glu Leu Lys Asn
65                  70                  75                  80

Ala Glu Thr Ala Ser Gly Glu Arg Tyr Ala Asp Glu Ala Gly Asn Glu
                85                  90                  95

Val Ala Met Lys Gly Ala Glu Gly Ile Leu Thr Leu Gly Asp Leu Lys
                100                 105                 110

Glu Val Pro Val Thr Val Glu Ala Lys
            115                 120

<210> SEQ ID NO 2
<211> LENGTH: 366
<212> TYPE: DNA
<213> ORGANISM: Fusobacterium nucleatum

<400> SEQUENCE: 2
atgagtttat tcttagtagc ttgtggagaa aaaaagaag aagaaaaacc agctgaacaa      60
```

```
gctgctgtag aagcaactgc aactgaagca cctgctacag aaacaactga agctgctgct    120
gaagctaaaa cattctcact taaaactgaa gatggaaaag aattcacatt agtagttgct    180
gctgatggaa gtactgcaac tttaactgat gcagaaggaa aagcaactga attaaaaaat    240
gctgaaactg catctggaga aagatatgca gatgaagctg gaaacgaagt tgctatgaaa    300
ggtgcagaag gaatcttaac tttaggagac cttaagaag taccagtaac tgttgaagct    360
aaatag                                                               366
```

```
<210> SEQ ID NO 3
<211> LENGTH: 130
<212> TYPE: PRT
<213> ORGANISM: Fusobacterium nucleatum

<400> SEQUENCE: 3
```

```
Met Lys Lys Ile Leu Leu Leu Ser Ser Leu Phe Leu Phe Ala Cys
1               5                   10                  15

Ala Asn Ile Asp Thr Gly Val Asp Glu Ser Lys Glu Ala Gln Ile Ser
            20                  25                  30

Arg Leu Leu Lys Glu Ala Asp Lys Lys Glu Lys Thr Val Glu Val
        35                  40                  45

Glu Lys Lys Leu Val Thr Asp Asn Gly Glu Glu Val Ile Glu Glu Glu
    50                  55                  60

Ala Thr Val Gln Asn Lys Lys Ser His Lys Gly Met Thr Arg Gly Glu
65                  70                  75                  80

Ile Met Glu Tyr Glu Met Thr Arg Val Ser Asp Glu Met Asn Ala Leu
                85                  90                  95

Gln Ala Asp Val Gln Gln Tyr Gln Glu Lys Lys Ala Gln Leu Lys Ala
            100                 105                 110

Tyr Gln Glu Lys Leu Gln Lys Leu Glu Glu Leu Ile Asn Asn Ala Gly
        115                 120                 125

Ile Lys
    130
```

```
<210> SEQ ID NO 4
<211> LENGTH: 390
<212> TYPE: DNA
<213> ORGANISM: Fusobacterium nucleatum

<400> SEQUENCE: 4
```

```
ttgaaaaaaa tattattact attatcttct ttattttat ttgcttgtgc taatatagat     60
acaggtgtag atgaaagtaa agaagctcaa atatcaagac ttttaaaaga agctgataag    120
aaaaaagaaa aaacagtaga agtagaaaag aaacttgtaa ctgataatgg agaggaagtt    180
atagaggaag aagctaccgt tcaaaacaaa aaatcacata aaggaatgac aagaggggaa    240
ataatggaat atgaaatgac aagagtttca gatgaaatga atgccctaca agcggatgta    300
caacaatatc aagaaagaa agcacaacta aaagcatacc aagaaaaatt acaaaaatta    360
gaagaattaa ataatgcagg aataaaataa                                    390
```

```
<210> SEQ ID NO 5
<211> LENGTH: 123
<212> TYPE: PRT
<213> ORGANISM: Fusobacterium nucleatum

<400> SEQUENCE: 5
```

```
Met Lys Lys Val Ile Leu Thr Leu Phe Val Leu Leu Ser Ile Gly Ile
1               5                   10                  15
```

Phe Ala Asn Asp Glu Ile Ile Ser Glu Leu Lys Gly Leu Asn Ala Glu
            20                  25                  30

Tyr Glu Asn Leu Val Lys Glu Glu Ala Arg Phe Gln Lys Glu Lys
        35                  40                  45

Glu Leu Ser Glu Arg Ala Ala Ala Gln Asn Val Lys Leu Ala Glu Leu
    50                  55                  60

Lys Ala Ser Ile Glu Glu Lys Leu Leu Ala Ala Pro Glu Glu Arg Lys
65                  70                  75                  80

Thr Lys Phe Phe Lys Asp Thr Phe Asp Gly Leu Val Lys Asp Tyr Ser
                85                  90                  95

Lys Tyr Leu Ser Gln Ile Asn Glu Lys Ile Ala Glu Asn Thr Glu Ile
            100                 105                 110

Val Ser Asn Phe Glu Lys Ile Gln Lys Ile Arg
        115                 120

<210> SEQ ID NO 6
<211> LENGTH: 372
<212> TYPE: DNA
<213> ORGANISM: Fusobacterium nucleatum

<400> SEQUENCE: 6
atgaaaaaag ttattttaac attatttgtt ttattatcta ttggaatatt tgcaaatgat      60
gagattattt cagagttaaa aggacttaat gctgagtatg aaaatttagt aaaagaagaa     120
gaagctagat tcaaaaagaa aaagaacttt ctgaaagag cagcagctca aatgttaaa      180
ttggctgaat aaaagcaag cattgaagaa aaattgttag cagctccaga agaaagaaaa     240
acaaaatttt taagatac ttttgatggt ttagtgaaag attattcaaa atatttaagt      300
caaataaatg aaaaaatagc tgaaaatact gaaatagtaa gtaattttga aaaaattcaa    360
aaaataagat ag                                                         372

<210> SEQ ID NO 7
<211> LENGTH: 129
<212> TYPE: PRT
<213> ORGANISM: Fusobacterium nucleatum

<400> SEQUENCE: 7

Met Lys Lys Phe Leu Leu Leu Ala Val Leu Ala Val Ser Ala Ser Ala
1               5                   10                  15

Phe Ala Ala Asn Asp Ala Ala Ser Leu Val Gly Glu Leu Gln Ala Leu
            20                  25                  30

Asp Ala Glu Tyr Gln Asn Leu Ala Asn Gln Glu Glu Ala Arg Phe Asn
        35                  40                  45

Glu Glu Arg Ala Gln Ala Asp Ala Ala Arg Gln Ala Leu Ala Gln Asn
    50                  55                  60

Glu Gln Val Tyr Asn Glu Leu Ser Gln Arg Ala Gln Arg Leu Gln Ala
65                  70                  75                  80

Glu Ala Asn Thr Arg Phe Tyr Lys Ser Gln Tyr Gln Asp Leu Ala Ser
                85                  90                  95

Lys Tyr Glu Asp Ala Leu Lys Lys Leu Glu Ser Glu Met Glu Gln Gln
            100                 105                 110

Lys Ala Ile Ile Ser Asp Phe Glu Lys Ile Gln Ala Leu Arg Ala Gly
        115                 120                 125

Asn

```
<210> SEQ ID NO 8
<211> LENGTH: 390
<212> TYPE: DNA
<213> ORGANISM: Fusobacterium nucleatum

<400> SEQUENCE: 8
atgaaaaaat ttttattatt agcagtatta gctgtttctg cttcagcatt cgcagcaaat      60
gatgcagcaa gtttagtagg tgaattacaa gcattagatg ctgaatacca aaacttagca     120
aatcaagaag aagcaagatt caatgaagaa agagcacaag ctgacgctgc tagacaagca     180
ctagcacaaa atgaacaagt ttacaatgaa ttatctcaaa gagctcaaag acttcaagct     240
gaagctaaca caagatttta taaatctcaa taccaagatc tagcttctaa atatgaagac     300
gctttaaaga aattagaatc tgaaatggaa caacaaaaag ctattatttc tgattttgaa     360
aaaattcaag ctttaagagc tggtaactaa                                      390
```

DEFENSIN-INDUCING AGENTS

RELATED APPLICATIONS

This application is a national stage filing under 35 U.S.C. 371 of International Application PCT/US2003/040221, filed Dec. 15, 2003, which claims priority from U.S. Application No. 60/433,100, filed Dec. 13, 2002, the specification of which is incorporated by reference herein. International Application PCT/US2003/040221 was published under PCT Article 21(2) in English.

FUNDING

Work described herein was funded, in part, by NIH grant RO-1 DE12589. The United States government has certain rights in the invention.

BACKGROUND

Skin and mucosa have always been regarded as physical barriers to the outside environment; protecting the host from noxious intruders. Recent findings have led to the realization that these barriers are not only physical; they generate potent antimicrobial peptides (APs). These ancient compounds, first described in drosophila, are now known to be important for the "innate" immune system of a eukaryotic host. Antimicrobial peptides act on a broad spectrum of pathogens. The innate immune system works in conjunction with the adaptive immune system in mammals, by permitting the host to curb, delay, or avoid microbial growth shortly after an infection. Innate responses occur in a matter of hours, well before the acquired immune system can be sufficiently mobilized.

The defensin peptides are a superfamily of peptide antibiotics with a characteristic beta-sheet structure stabilized by two to three intramolecular disulfide bonds. They are strongly cationic by virtue of their numerous arginine and lysine residues. The amphipathic and cationic characteristics are important for antibacterial activity. Defensin peptides have been isolated from a number of phagocytes from mammals including humans, and various tissue and fluid sources such as mammalian trachea, intestine, tongue, human oral gingiva, human organs, plasma and urine.

The human defensin AP family is roughly divided into two subfamilies; alpha-defensins, found in azurophilic granules of PMNs and in the granules of Paneth cells found in the base of the crypts of Lieberklühn in the small intestine, and the beta-defensins, expressed generally by epithelial cells. The alpha- and beta-defensins differ in primary sequence and in the placement of the three disulfide bonds. The signature motif for beta-defensin genes includes two exons surrounding a variably sized intron. Exon 1 encodes the signal sequence, while exon 2 encodes the propeptide and mature peptide. This motif differs from that found in alpha-defensin genes in that the latter are organized with three exons and two introns. Other differentiating features between alpha- and beta-defensins include the fact that while the former are cytotoxic to mammalian cells when released from protective granules, the latter are not.

In addition to demonstrating antibacterial and antifungal properties, beta-defensins engage the CCR6 receptor on selected immune effector cells, such as immature dendritic cells and T cells and evoke a chemokine response, thereby recruiting these cells to the site of interest.

The growing problem of resistance to conventional antibiotics and the need for new antibiotics has stimulated interest in the development of antimicrobial peptides (APs) as therapeutics for humans and other animals. Unlike conventional antibiotics, acquisition of resistance by a sensitive organism against APs is surprisingly rare and difficult to generate.

Accordingly, it would be desirable to have compositions and methods for causing cells to increase production of beta-defensins.

BRIEF SUMMARY

In certain aspects the application provides polypeptides and compositions that stimulate production of defensins, preferably in epithelial cells. In certain embodiments, the application provides *Fusobacterium* Associated Defensin Inducer polypeptides (FAD-I). In further embodiments, the application provides defensin-stimulating compositions comprising a FAD-I and an excipient.

In certain embodiments, a FAD-I polypeptide is a polypeptide that comprises an amino acid sequence that is at least 90%, 95%, 97%, 99% or 100% identical to the amino acid sequence of SEQ ID NOs.:1, 3, 5, or 7. In certain embodiments, a FAD-I polypeptide is a polypeptide comprising a portion of an amino acid sequence that is at least 90%, 95%, 97%, 99% or 100% identical to SEQ ID NOs.:1, 3, 5, or 7, wherein said portion is sufficient to induce beta-defensin-2 (BD-2) production, beta-defensin-3 (BD-3) production, or both, and preferably induction of human beta-defensin-2 (hBD-2) production, human beta-defensin-3 (hBD-3) production, or both. In certain embodiments a FAD-I polypeptide is a polypeptide obtained when a nucleic acid comprising a nucleic acid sequence at least 90%, 95%, 97%, 99% or 100% identical to a nucleic acid sequence of SEQ ID NOs.:2, 4, 6, or 8 is expressed in cell, preferably a bacterial cell, such as *F. nucleatum* or *E. coli*. In certain embodiments, a FAD-I polypeptide is a polypeptide derived from a *F. nucleatum* cell wall, having a monomeric molecular weight range of about 12-14 kDa and which polypeptide induces BD-2 production, BD-3 production, or both. In certain embodiments, the FAD-I polypeptide additionally has a pI of between 4.0 and 5.5. In certain embodiments a FAD-I polypeptide is purified or partially purified. In preferred embodiments, the FAD-I polypeptide and/or a composition comprising the FAD-I polypeptide induces beta-defensin production in at least one epithelial cell type, such as an oral epithelial cell, a corneal epithelial cell, a skin cell. In preferred embodiments, the defensin induced is a BD-2, a BD-3, or both, and in humans, an hBD2, an hBD3, or both. In certain embodiments, the FAD-I polypeptide and/or composition comprising the FAD-I polypeptide induces beta-defensin production in one or more cells of a mucosal epithelium, such as the vagina, rectum, urethra, intestines, nasal epithelium, oral epithelium or corneal epithelium.

In certain embodiments, the defensin-stimulating composition is formulated for delivery systemically, as to the bloodstream. In certain embodiments, the defensin-stimulating composition is formulated for local delivery, such as to a particular epithelium, optionally a mucosal epithelium. For example, a composition may be formulated for delivery to the mouth, the eye, the skin, the vagina, the rectum, the intestines and the nose or other airways. In certain embodiments, the application provides methods for making a medicament comprising a FAD-I and an excipient for the administration by one of the above-described modes.

In certain embodiments, the application provides methods for treating a variety of diseases by administering a defensin-inducing composition comprising a FAD-I. Examples of diseases to be treated include infectious diseases of the various epithelial tissues, including conjunctivitis, gingivitis, tooth decay, sinusitis, urinary tract infections, gastroenteritis and dermatitis, any of which may be bacterial, fungal or viral in origin. Diseases to be treated include systemic infectious diseases as well. In certain embodiments, compositions comprising an FAD-I may be used to treat infections that are resistant to one or more other antimicrobial agents, such as vancomycin resistant *Enterococcus* or methicillin resistant *Staphylococcus aureus*, penicillin or cephalosporin resistant *Pneumococcus*, multi-drug resistant *Pseudomonas*, to name only a few. Cancers may also be treated using compositions disclosed herein, including squamous cell carcinomas, such as oral squamous cell carcinomas, and other tumor types.

In certain embodiments, a composition comprising a FAD-I polypeptide further comprises additional reagents, such as antibacterial agents, antifungal agents, antiviral agents and chemotherapeutic agents.

In certain aspects the application provides methods for stimulating BD-2 production, BD-3 production, or both, comprising contacting a cell with a composition comprising a FAD-I. In certain preferred embodiments, the cell is an epithelial cell, optionally an epithelial cell located in a vertebrate such as a human. In certain exemplary embodiments, the epithelial cell is an oral epithelial cell, a corneal epithelial cell or a keratinocyte. In certain embodiments, the epithelial cell is a mucosal epithelial cell.

In certain aspects the application provides isolated and/or recombinant nucleic acid constructs comprising a nucleic acid encoding a FAD-I. In certain embodiments a recombinant nucleic acid comprises a nucleic acid that is at least 90%, 95%, 97%, 99% or 100% identical to a nucleic acid of SEQ ID NOs.:2, 4, 6, or 8, operably linked to a promoter. In preferred embodiments, the nucleic acid construct is designed to permit production of FAD-I polypeptide in a host cell, such as a bacterium (e.g. *F. nucleatum* or *E. coli*), a yeast cell, an insect cell or mammalian cell. In certain aspects the application provides methods for producing a FAD-I comprising expressing a recombinant nucleic acid construct disclosed herein and obtaining the produced FAD-I polypeptide. Preferably the methods further comprise one or more purification steps.

In certain aspects, the application provides methods of screening for agents that induce an innate immune response in a human comprising providing a cellular extract of a commensal microorganism and determining a change in the innate immune response of an organism or cell. In certain embodiments, the commensal microorganism is a BD-2 or BD-3 resistant bacterium. In certain embodiments, the change in the innate immune response is stimulation of BD-2 or BD-3 or both expression in a cell.

The embodiments and practices of the present invention, other embodiments, and their features and characteristics, will be apparent from the description, figures and claims that follow, with all of the claims hereby being incorporated by this reference into this Summary.

BRIEF DESCRIPTION OF THE DRAWINGS

FIG. 1A, peak I; FIG. 1B, Lane 1=void volume; FIG. 1A, peak II; FIG. 1B, Lane 2=fraction eluting at 36% acetonitrile; FIG. 1A, *, arrow; FIG. 1B, Lane 3=fraction eluting between 47-50% acetonitrile.

DETAILED DESCRIPTION

Figure 1:
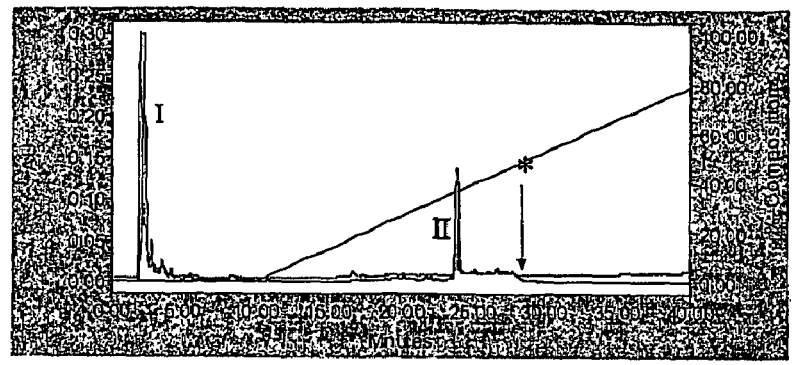
FIG. 1. HPLC fractionation of *F. nucleatum* cell wall soluble supernatant followed by Normal Human Oral Epithelial Cell (NHOEC) monolayer challenge and RT-PCR analysis of hBD-2 mRNA induction. Untreated *F. nucleatum* cell wall soluble supernatant was charged onto a C4 HPLC column and fractions were eluted based on acetonitrile concentrations. After concentration and acetonitrile dissipation, respective fractions were incubated with NHOEC monolayers, overnight. RT-PCR analysis revealed that the shoulder eluting at 47-55% acetonitrile (A; asterisk, arrow) (B, lane 3) induced hBD-2 mRNA, while the other fractions (FIG. 1A; I, II) did not.
Figure 1:
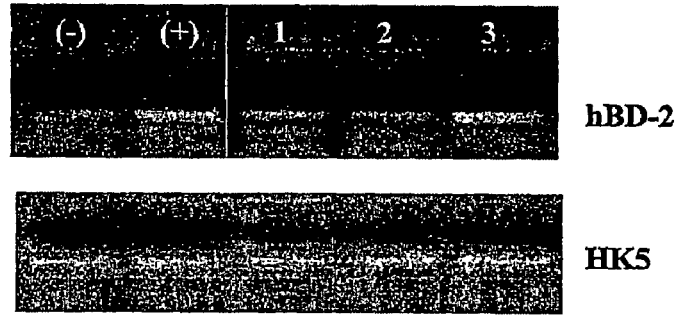

1. Definitions:

For convenience, certain terms employed in the specification, examples, and appended claims are collected here. Unless defined otherwise, all technical and scientific terms used herein have the same meaning as commonly understood by one of ordinary skill in the art to which this invention belongs.

The articles "a" and "an" are used herein to refer to one or to more than one (i.e., to at least one) of the grammatical object of the article. By way of example, "an element" means one element or more than one element.

A "chimeric polypeptide" or "fusion polypeptide" is a fusion of a first amino acid sequence with a second amino acid sequence where the first and second amino acid sequences are not naturally present in a single polypeptide chain.

An "expression construct" is any recombinant nucleic acid that includes an expressible nucleic acid and regulatory elements sufficient to mediate expression in a suitable host cell. For example, an expression construct may contain a promoter or other RNA polymerase contact site, a transcription start site or a transcription terrmination sequence. An expression construct for production of a protein may contain a translation start site, such as an ATG codon, a ribosome binding site, such as a Shine-Dalgarno sequence, or a translation stop codon.

The term "heterologous" as used in describing a nucleic acid with respect to another nucleic acid means that the two nucleic acids are not normally operably linked to each other or do not naturally occur in adjacent positions.

The term "including" is used herein to mean, and is used interchangeably with, the phrase "including but not limited to."

The term "nucleic acid" refers to polynucleotides such as deoxyribonucleic acid (DNA), and, where appropriate, ribonucleic acid (RNA). The term should also be understood to include, as equivalents, analogs of either RNA or DNA made from nucleotide analogs, and, as applicable to the embodiment being described, single (sense or antisense) and double-stranded polynucleotides.

The term "or" is used herein to mean, and is used interchangeably with, the term "and/or", unless context clearly indicates otherwise.

The term "percent identical" refers to sequence identity between two amino acid sequences or between two nucleotide sequences. Identity can each be determined by comparing a position in each sequence which may be aligned for purposes of comparison. When an equivalent position in the compared sequences is occupied by the same base or amino acid, then the molecules are identical at that position; when the equivalent site occupied by the same or a similar amino acid residue (e.g., similar in steric and/or electronic nature), then the molecules can be referred to as homologous (similar) at that position. Expression as a percentage of homology/similarity or identity refers to a function of the number of identical or similar amino acids at positions shared by the compared sequences. Various alignment algorithms and/or programs may be used, including FASTA, BLAST or ENTREZ. FASTA and BLAST are available as a part of the GCG sequence analysis package (University of Wisconsin, Madison, Wis.), and can be used with, e.g., default settings: ENTREZ is available through the National Center for Biotechnology Information, National Library of Medicine, National Institutes of Health, Bethesda, Md. In one embodiment, the percent identity of two sequences can be determined by the GCG program with a gap weight of 1, e.g., each amino acid gap is weighted as if it were a single amino acid or nucleotide mismatch between the two sequences.

The terms "polypeptide" and "protein" are used interchangeably herein.

The term "purified protein" refers to a preparation of a protein or proteins which are preferably isolated from, or otherwise substantially free of, other proteins normally associated with the protein(s) in a cell or cell lysate. The term "substantially free of other cellular proteins" (also referred to herein as "substantially free of other contaminating proteins") is defined as encompassing individual preparations of each of the component proteins comprising less than 20% (by dry weight) contaminating protein, and preferably comprises less than 5% contaminating protein. Functional forms of each of the component proteins can be prepared as purified preparations by using a cloned gene as described in the attached examples. By "purified", it is meant, when referring to component protein preparations used to generate a reconstituted protein mixture, that the indicated molecule is present in the substantial absence of other biological macromolecules, such as other proteins (particularly other proteins which may substantially mask, diminish, confuse or alter the characteristics of the component proteins either as purified preparations or in their function in the subject reconstituted mixture). The term "purified" as used herein preferably means at least 80% by dry weight, more preferably in the range of 85% by weight, more preferably 95-99% by weight, and most preferably at least 99.8% by weight, of biological macromolecules of the same type present (but water, buffers, and other small molecules, especially molecules having a molecular weight of less than 5000, can be present). The term "pure" as used herein preferably has the same numerical limits as "purified" immediately above.

The term "recombinant nucleic acid construct" includes any nucleic acid comprising at least two sequences which are not present together in nature. A recombinant nucleic acid may be generated in vitro, for example by using the methods of molecular biology, or in vivo, for example by insertion of a nucleic acid at a novel chromosomal location by homologous or non-homologous recombination.

The term "beta-defensin (BD) associated disorder" is a disorder and/or condition in response to which production of BD, such as for example, BD-2 and/or BD-3, is induced in a host afflicted with said disorder or condition. In certain embodiments, said condition may be an infection caused by a bacterium, a fungus, or a virus.

2. Defensin-stimulating Polypeptides

In certain aspects, the present disclosure makes available isolated and/or purified forms of the subject FAD-I polypeptides, which are isolated from, or otherwise substantially free of, other proteins which might normally be associated with the protein or a particular complex including the protein. In certain embodiments, FAD-I polypeptides are formulated into a composition comprising a FAD-I polypeptide and an excipient. In certain embodiments, a FAD-I polypeptide is a polypeptide that comprises an amino acid sequence that is at least 90%, 95%, 97%, 99% or 100% identical to the amino acid sequence of SEQ ID NOs.: 1, 3, 5, or 7. In certain embodiments, a FAD-I polypeptide is a polypeptide comprising a portion of an amino acid sequence that is at least 90%, 95%, 97%, 99% or 100% identical to SEQ ID NOs.: 1, 3, 5, or 7, wherein said portion is sufficient to induce BD-2 production, BD-3 production, or both, and preferably induction of hBD-2 production, hBD-3 production, or both. In certain embodiments a FAD-I polypeptide is a polypeptide obtained by expressing a nucleic acid comprising a nucleic acid sequence at least 90%, 95%, 97%, 99% or 100% identical to a nucleic acid sequence of SEQ ID NOs.:2, 4, 6, or 8 in cell, preferably a bacterial cell, such as *F. nucleatum* or *E. coli*. In certain embodiments, a FAD-I polypeptide is a polypeptide derived from a *F. nucleatum* cell wall, having a monomeric molecular weight range of about 12-14 kDa and which polypeptide induces BD-2 production, BD-3 production, or both. In certain embodiments, the FAD-I polypeptide additionally has a pI of between 4.0 and 5.5. In certain embodiments a FAD-I polypeptide is purified or partially purified. In preferred embodiments, the FAD-I polypeptide and/or a composition comprising the FAD-I polypeptide induces beta-defensin production in at least one epithelial cell type, such as an oral epithelial cell, a corneal epithelial cell, a skin cell. In preferred embodiments, the defensin induced is a BD-2, a BD-3, or both, and in humans, an hBD2, an hBD3, or both. In certain embodiments, the FAD-I polypeptide and/or

| Gene Name[1] | Pre-protein[2] | | Mature[3] | | Function | % Indentity[4] |
|---|---|---|---|---|---|---|
| | kDA | pI | kDa | pI | | |
| FN0264 | 14.5 | 4.8 | 12.6 | 4.6 | Fad-A | 75% |
| FN1529 | 14.2 | 5.4 | 12.2 | 5.1 | Hypothetical FAD-I | 67% |
| FN1792 | —[5] | —[5] | 12.5 | 4.3 | Hypothetical FAD-I | 65% & 39% |
| FN1527 | 14.8 | 5.4 | 13.1 | 4.8 | Hypothetical FAD-I | 33% | composition comprising the FAD-I polypeptide induces beta-defensin production in one or more cells of a mucosal epithelium, such as the vagina, rectum, urethra, intestines, nasal epithelium, oral epithelium or corneal epithelium.

(NP_602592)
SEQ ID NO.:1
MSLFLVACGEKKEEEKPAEQAAVEATATEAPATETTEAAAEAKTFSLKTE

DGKEFTLVVAADGSTATLTDAEGKATELKNAETASGERYADEAGNEVAMK

GAEGILTLGDLKEVPVTVEAK (NP_602354)
SEQ ID NO.:3
MKKILLLLSSLFLFACANIDTGVDESKEAQISRLLKEADKKKEKTVEVEK

KLVTDNGEEVIEEEATVQNKKSHKGMTRGEIMEYEMTRVSDEMNALQADV

QQYQEKKAQLKAYQEKLQKLEELINNAGIK (NP_602356)
SEQ ID NO.:5
MKKVILTLFVLLSIGIFANDEIISELKGLNAEYENLVKEEEARFQKEKEL

SERAAAQNVKLAELKASIEEKLLAAPEERKTKFFKDTFDGLVKDYSKYLS

QINEKIAENTEIVSNFEKIQKIR (NP_603171)
SEQ ID NO.:7
MKKFLLLAVLAVSASAFAANDAASLVGELQALDAEYQNLANQEEARFNEE

RAQADAARQALAQNEQVYNELSQRAQRLQAEANTRFYKSQYQDLASKYED

ALKKLESEMEQQKAIISDFEKIQALRAGN

Table 1. Predicted Physical Properties of FAD-I Polypeptides. 1: Gene name; taken from the *F. nucleatum* ATCC 25586 genome (Kapatral et al., 2002, J. Bacteriol. 184 (7), 2005-2018); 2: Preprotein; designation of entire protein, containing the signal peptide; 3: Mature protein; designation of the protein without the signal peptide; 4:% identity; % of matched peptide sequence of entire protein; 5: no signal peptide found.

Another aspect of the disclosure relates to polypeptides derived from a full-length FAD-I polypeptide. Isolated peptidyl portions of the subject proteins can be obtained by screening polypeptides recombinantly produced from the corresponding fragment of the nucleic acid encoding such polypeptides. In addition, fragments can be chemically synthesized using techniques known in the art such as conventional Merrifield solid phase f-Moc or t-Boc chemistry. For example, any one of the subject proteins can be arbitrarily divided into fragments of desired length with no overlap of the fragments, or preferably divided into overlapping fragments of a desired length. The fragments can be produced (recombinantly or by chemical synthesis) and tested to identify those peptidyl fragments which can function in a cellular assay for BD-2 induction, BD-3 induction, or both.

It is also possible to modify the structure of the subject FAD-I polypeptides for such purposes as enhancing therapeutic or prophylactic efficacy, or stability (e.g., ex vivo shelf life and resistance to proteolytic degradation in vivo). Such modified polypeptides, when designed to retain at least one activity of the naturally-occurring form of the protein, are considered functional equivalents of the FAD-I polypeptides described in more detail herein. Such modified polypeptides can be produced, for instance, by amino acid substitution, deletion, or addition.

For instance, it is reasonable to expect, for example, that an isolated replacement of a leucine with an isoleucine or valine, an aspartate with a glutamate, a threonine with a serine, or a similar replacement of an amino acid with a structurally related amino acid (i.e. conservative mutations) will not have a major effect on the biological activity of the resulting molecule. Conservative replacements are those that take place within a family of amino acids that are related in their side chains. Genetically encoded amino acids are can be divided into four families: (1) acidic=aspartate, glutamate; (2) basic=lysine, arginine, histidine; (3) nonpolar=alanine, valine, leucine, isoleucine, proline, phenylalanine, methionine, tryptophan; and (4) uncharged polar=glycine, asparagine, glutamine, cysteine, serine, threonine, tyrosine. Phenylalanine, tryptophan, and tyrosine are sometimes classified jointly as aromatic amino acids. In similar fashion, the amino acid repertoire can be grouped as (1) acidic=aspartate, glutamate; (2) basic=lysine, arginine histidine, (3) aliphatic=glycine, alanine, valine, leucine, isoleucine, serine, threonine, with serine and threonine optionally be grouped separately as aliphatic-hydroxyl; (4) aromatic=phenylalanine, tyrosine, tryptophan; (5) amide=asparagine, glutamine; and (6) sulfur-containing=cysteine and methionine. (see, for example, Biochemistry, 2nd ed., Ed. by L. Stryer, W.H. Freeman and Co., 1981). Whether a change in the amino acid sequence of a polypeptide results in a functional homolog can be readily determined by assessing the ability of the variant polypeptide to produce a response in cells in a fashion similar to the wild-type protein. For instance, such variant forms of a FAD-I polypeptide can be assessed, e.g., for their ability induce BD-2 production, BD-3 production, or both in a cell. Polypeptides in which more than one replacement has taken place can readily be tested in the same manner.

This invention further contemplates a method of generating sets of combinatorial mutants of the subject FAD-I polypeptides, as well as truncation mutants. The purpose of screening such combinatorial libraries is to generate, for example, FAD-I homologs which can act as either agonists or antagonist, or alternatively, which possess novel activities all together. Combinatorially-derived homologs can be generated which have a selective potency relative to a naturally occurring FAD-I polypeptide. Such proteins, when expressed from recombinant DNA constructs, can be used in gene therapy protocols.

Likewise, mutagenesis can give rise to homologs which have intracellular half-lives dramatically different than the corresponding wild-type protein. For example, the altered protein can be rendered either more stable or less stable to proteolytic degradation or other cellular process which result in destruction of, or otherwise inactivation of the FAD-I polypeptide of interest.

In similar fashion, FAD-I homologs can be generated by the present combinatorial approach to act as antagonists, in that they are able to interfere with the ability of the corresponding wild-type protein to function.

In a representative embodiment of this method, the amino acid sequences for a population of FAD-I homologs are aligned, preferably to promote the highest homology possible. Such a population of variants can include, for example, homologs from one or more species of *Fusobacterium*, or homologs from the same species but which differ due to mutation. Amino acids which appear at each position of the aligned sequences are selected to create a degenerate set of combinatorial sequences. In a preferred embodiment, the combinatorial library is produced by way of a degenerate library of genes encoding a library of polypeptides which each include at least a portion of potential FAD-I sequences. For instance, a mixture of synthetic oligonucleotides can be enzymatically ligated into gene sequences such that the degenerate set of potential BD-2 or BD-3 nucleotide sequences are expressible as individual polypeptides, or alternatively, as a set of larger fusion proteins (e.g. for phage display).

There are many ways by which the library of potential homologs can be generated from a degenerate oligonucleotide sequence. Chemical synthesis of a degenerate gene sequence can be carried out in an automatic DNA synthesizer, and the synthetic genes then be ligated into an appropriate gene for expression. The purpose of a degenerate set of genes is to provide, in one mixture, all of the sequences encoding the desired set of potential FAD-I sequences. The synthesis of degenerate oligonucleotides is well known in the art (see for example, Narang, S A (1983) Tetrahedron 39:3; Itakura et al., (1981) Recombinant DNA, Proc. 3rd Cleveland Sympos. Macromolecules, ed. A G Walton, Amsterdam: Elsevier pp 273-289; Itakura et al., (1984) Annu. Rev. Biochem. 53:323; Itakura et al., (1984) Science 198:1056; Ike et al., (1983) Nucleic Acid Res. 11:477). Such techniques have been employed in the directed evolution of other proteins (see, for example, Scott et al., (1990) Science 249:386-390; Roberts et al., (1992) PNAS USA 89:2429-2433; Devlin et al., (1990) Science 249: 404-406; Cwirla et al., (1990) PNAS USA 87: 6378-6382; as well as U.S. Pat. Nos. 5,223,409, 5,198,346, and 5,096,815).

Alternatively, other forms of mutagenesis can be utilized to generate a combinatorial library. For example, FAD-I variants can be generated and isolated from a library by screening using, for example, alanine scanning mutagenesis and the like (Ruf et al., (1994) Biochemistry 33:1565-1572; Wang et al., (1994) J. Biol. Chem. 269:3095-3099; Balint et al., (1993)

Gene 137:109-118; Grodberg et al., (1993) Eur. J. Biochem. 218:597-601; Nagashima et al., (1993) J. Biol. Chem. 268: 2888-2892; Lowman et al., (1991) Biochemistry 30:10832-10838; and Cunningham et al., (1989) Science 244:1081-1085), by linker scanning mutagenesis (Gustin et al., (1993) Virology 193:653-660; Brown et al., (1992) Mol. Cell Biol. 12:2644-2652; McKnight et al., (1982) Science 232:316); by saturation mutagenesis (Meyers et al., (1986) Science 232: 613); by PCR mutagenesis (Leung et al., (1989) Method Cell Mol Biol 1:11-19); or by random mutagenesis, including chemical mutagenesis, etc. (Miller et al., (1992) A Short Course in Bacterial Genetics, CSHL Press, Cold Spring Harbor, N.Y.; and Greener et al., (1994) Strategies in Mol Biol 7:32-34). Linker scanning mutagenesis, particularly in a combinatorial setting, is an attractive method for identifying truncated and bioactive variants of FAD-I polypeptides.

A wide range of techniques are known in the art for screening gene products of combinatorial libraries made by point mutations and truncations, and, for that matter, for screening cDNA libraries for gene products having a certain property. Such techniques will be generally adaptable for rapid screening of the gene libraries generated by the combinatorial mutagenesis of FAD-I variants. The most widely used techniques for screening large gene libraries typically comprises cloning the gene library into replicable expression vectors, transforming appropriate cells with the resulting library of vectors, and expressing the combinatorial genes under conditions in which detection of a desired activity facilitates relatively easy isolation of the vector encoding the gene whose product was detected. Each of the illustrative assays described below are amenable to high through-put analysis as necessary to screen large numbers of degenerate sequences created by combinatorial mutagenesis techniques.

FAD-I polypeptides may further comprise post-translational or non-amino acid elements, such as hydrophobic modifications (e.g. polyethylene glycols or lipids), poly- or mono-saccharide modifications, phosphates, acetylations, etc. Effects of such elements on the functionality of a FAD-I polypeptide may be tested as described herein for other FAD-I variants.

The disclosure further provides methods for testing the functionality of FAD-I polypeptides, variants and fragments. In general, cells may be transfected with a BD-2 or BD-3 reporter construct, wherein a FAD-I responsive regulatory element of a BD-2 or BD-3 gene is operably linked to a reporter gene, and preferably a reporter gene that produces a fluorescent protein (e.g. green fluorescent protein) or an enzyme that can generate a fluorescent substrate. The cells are then contacted with the FAD-I polypeptide and reporter gene expression is assessed. In certain embodiments, an assay may comprise employing a cell that naturally has inducible expression of BD-2, BD-3, or both, such as a normal human oral epithelial cell. The cell may be transfected with a reporter construct or the expression of normal BD-2 transcript, BD-3 transcript, or both, or polypeptide thereof may be assessed.

3. Nucleic Acids

In certain aspects the invention provides isolated and/or recombinant nucleic acids encoding FAD-I polypeptides, such as, for example, SEQ ID NOs.: 2, 4, 6, or 8. Nucleic acids of the invention are further understood to include nucleic acids that comprise variants of SEQ ID NOs.: 2, 4, 6, or 8. Variant nucleotide sequences include sequences that differ by one or more nucleotide substitutions, additions or deletions, such as allelic variants; and will, therefore, include coding sequences that differ from the nucleotide sequence of the coding sequence designated in SEQ ID NOs.: 2, 4, 6, or 8, e.g. due to the degeneracy of the genetic code. For example, nucleic acids encoding FAS-I polypeptides may be nucleic acids comprising a sequence that is at least 90%, 95%, 99% or 10% identical to the sequence of SEQ ID NOs.: 2, 4, 6, or 8, or a sequence that encodes the polypeptide of SEQ ID NOs.:1, 3, 5, 6, or 7. In other embodiments, variants will also include sequences that will hybridize under highly stringent conditions to a coding sequence of a nucleic acid sequence designated in SEQ ID NOs.: 2, 4, 6, or 8.

```
SEQ ID NO.:2 (Nucleotides 272989-273354 of
NC_003454):
ATGAGTTTATTCTTAGTAGCTTGTGGAGAAAAAAAGAAGAAGAAAAACC

AGCTGAACAAGCTGCTGTAGAAGCAACTGCAACTGAAGCACCTGCTACAG

AAACAACTGAAGCTGCTGCTGAAGCTAAAACATTCTCACTTAAAACTGAA

GATGGAAAAGAATTCACATTAGTAGTTGCTGCTGATGGAAGTACTGCAAC

TTTAACTGATGCAGAAGGAAAAGCAACTGAATTAAAAAATGCTGAAACTG

CATCTGGAGAAAGATATGCAGATGAAGCTGGAAACGAAGTTGCTATGAAA

GGTGCAGAAGGAATCTTAACTTTAGGAGACCTTAAAGAAGTACCAGTAAC

TGTTGAAGCTAAATAG

SEQ ID NO.:4 (Nucleotides 42273-42662 of
NC_003454):
TTGAAAAAAATATTATTACTATTATCTTCTTTATTTTTATTTGCTTGTGC

TAATATAGATACAGGTGTAGATGAAAGTAAAGAAGCTCAAATATCAAGAC

TTTTAAAAGAAGCTGATAAGAAAAAAGAAAAAACAGTAGAAGTAGAAAAG

AAACTTGTAACTGATAATGGAGAGGAAGTTATAGAGGAAGAAGCTACCGT

TCAAAACAAAAAATCACATAAAGGAATGACAAGAGGGGAAATAATGGAAT

ATGAAATGACAAGAGTTTCAGATGAAATGAATGCCCTACAAGCGGATGTA

CAACAATATCAAGAAAAGAAAGCACAACTAAAAGCATACCAAGAAAAATT

ACAAAAATTAGAAGAATTAAATAATGCAGGAATAAAATAA

SEQ ID NO.:6 (Nucleotides 43083-43454 of
NC_003454)
ATGAAAAAAGTTATTTTAACATTATTTGTTTTATTATCTATTGGAATATT

TGCAAATGATGAGATTATTTCAGAGTTAAAAGGACTTAATGCTGAGTATG

AAAATTTAGTAAAAGAAGAAGAAGCTAGATTTCAAAAAGAAAAAGAACTT

TCTGAAAGAGCAGCAGCTCAAAATGTTAAATTGGCTGAATTAAAAGCAAG

CATTGAAGAAAATTGTTAGCAGCTCCAGAAGAAAGAAAAACAAAATTTT

TTAAAGATACTTTTGATGGTTTAGTGAAAGATTATTCAAAATATTTAAGT

CAAATAAATGAAAAAATAGCTGAAAATACTGAAATAGTAAGTAATTTTGA

AAAAATTCAAAAAATAAGATAG

SEQ ID NO.:8 (Nucleotides 891002-891391 of
NC_003454)
ATGAAAAAATTTTATTATTAGCAGTATTAGCTGTTTCTGCTTCAGCATT

CGCAGCAAATGATGCAGCAAGTTTAGTAGGTGAATTACAAGCATTAGATG

CTGAATACCAAAACTTAGCAAATCAAGAAGAAGCAAGATTCAATGAAGAA
```

-continued
AGAGCACAAGCTGACGCTGCTAGACAAGCACTAGCACAAAATGAACAAGT

TTACAATGAATTATCTCAAAGAGCTCAAAGACTTCAAGCTGAAGCTAACA

CAAGATTTTATAAATCTCAATACCAAGATCTAGCTTCTAAATATGAAGAC

GCTTTAAAGAAATTAGAATCTGAAATGGAACAACAAAAAGCTATTATTTC

TGATTTTGAAAAAATTCAAGCTTTAAGAGCTGGTAACTAA

One of ordinary skill in the art will understand readily that appropriate stringency conditions which promote DNA hybridization can be varied. For example, one could perform the hybridization at 6.0× sodium chloride/sodium citrate (SSC) at about 45° C., followed by a wash of 2.0×SSC at 50° C. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C. Both temperature and salt may be varied, or temperature or salt concentration may be held constant while the other variable is changed. In one embodiment, the invention provides nucleic acids which hybridize under low stringency conditions of 6×SSC at room temperature followed by a wash at 2×SSC at room temperature.

Isolated nucleic acids which differ from SEQ ID NOs.: 2, 4, 6, or 8 due to degeneracy in the genetic code are also within the scope of the invention. For example, a number of amino acids are designated by more than one triplet. Codons that specify the same amino acid, or synonyms (for example, CAU and CAC are synonyms for histidine) may result in "silent" mutations which do not affect the amino acid sequence of the protein. However, it is expected that DNA sequence polymorphisms that do lead to changes in the amino acid sequences of the subject proteins will exist among Fusobacterium cultivars. One skilled in the art will appreciate that these variations in one or more nucleotides of the nucleic acids encoding a particular protein may exist among individuals of a given species due to natural allelic variation. Any and all such nucleotide variations and resulting amino acid polymorphisms are within the scope of this invention.

Optionally, a FAD-I nucleic acid of the invention will genetically complement a partial or complete FAD-I loss of function phenotype in an *F. nucleatum* cell. For example, a FAD-I nucleic acid of the invention may be expressed in a cell in which endogenous FAD-I has been knocked out, and the introduced FAD-I nucleic acid will mitigate a phenotype resulting from the knockout. An exemplary FAD-I loss of function phenotype is a decrease in the stimulation of hBD-2 expression, hBD-3 expression, or both in NHOECs or similarly sensitive cell types.

In certain aspects, nucleic acids encoding FAD-I polypeptides may be used to increase FAD-I expression in an organism or cell by direct delivery of the nucleic acid. A nucleic acid therapy construct of the present invention can be delivered, for example, as an expression plasmid which, when transcribed in the cell, produces RNA which encodes a FAD-I polypeptide.

In another aspect of the invention, the subject nucleic acid is provided in an expression vector comprising a nucleotide sequence encoding a subject FAD-I polypeptide and operably linked to at least one regulatory sequence. Regulatory sequences are art-recognized and are selected to direct expression of the FAD-I polypeptide. Accordingly, the term regulatory sequence includes promoters, enhancers and other expression control elements. Exemplary regulatory sequences are described in Goeddel; *Gene Expression Technology: Methods in Enzymology*, Academic Press, San Diego, Calif. (1990). For instance, any of a wide variety of expression control sequences that control the expression of a DNA sequence when operatively linked to it may be used in these vectors to express DNA sequences encoding a FAD-I polypeptide. Such useful expression control sequences, include, for example, the early and late promoters of SV40, tet promoter, adenovirus or cytomegalovirus immediate early promoter, the lac system, the trp system, the TAC or TRC system, T7 promoter whose expression is directed by T7 RNA polymerase, the major operator and promoter regions of phage lambda, the control regions for fd coat protein, the promoter for 3-phosphoglycerate kinase or other glycolytic enzymes, the promoters of acid phosphatase, e.g., Pho5, the promoters of the yeast α-mating factors, the polyhedron promoter of the baculovirus system and other sequences known to control the expression of genes of prokaryotic or eukaryotic cells or their viruses, and various combinations thereof. It should be understood that the design of the expression vector may depend on such factors as the choice of the host cell to be transformed and/or the type of protein desired to be expressed. Moreover, the vector's copy number, the ability to control that copy number and the expression of any other protein encoded by the vector, such as antibiotic markers, should also be considered.

As will be apparent, the subject gene constructs can be used to cause expression of the subject FAD-I polypeptides in cells propagated in culture, e.g. to produce proteins or polypeptides, including fusion proteins or polypeptides, for purification.

This invention also pertains to a host cell transfected with a recombinant gene including a coding sequence for one or more of the subject FAD-I polypeptides. The host cell may be any prokaryotic or eukaryotic cell. For example, a polypeptide of the present invention may be expressed in bacterial cells such as *E. coli*, insect cells (e.g., using a baculovirus expression system), yeast, or mammalian cells. Other suitable host cells are known to those skilled in the art.

Accordingly, the present invention further pertains to methods of producing the subject FAD-I polypeptides. For example, a host cell transfected with an expression vector encoding a FAD-I polypeptide can be cultured under appropriate conditions to allow expression of the polypeptide to occur. The polypeptide may be secreted and isolated from a mixture of cells and medium containing the polypeptide. Alternatively, the polypeptide may be retained cytoplasmically and the cells harvested, lysed and the protein isolated. A cell culture includes host cells, media and other byproducts. Suitable media for cell culture are well known in the art. The polypeptide can be isolated from cell culture medium, host cells, or both using techniques known in the art for purifying proteins, including ion-exchange chromatography, gel filtration chromatography, ultrafiltration, electrophoresis, and immunoaffinity purification with antibodies specific for particular epitopes of the polypeptide. In a preferred embodiment, the FAD-I polypeptide is a fusion protein containing a domain which facilitates its purification, such as a FAD-I-GST fusion protein, FAD-I-intein fusion protein, FAD-I-cellulose binding domain fusion protein, FAD-I-polyhistidine fusion protein etc.

Methods for purifying FAD-I from *F. nucleatum* cell wall extracts are also disclosed herein. See, e.g., Example 1.

A nucleotide sequence encoding a FAD-I polypeptide can be used to produce a recombinant form of the protein via microbial or eukaryotic cellular processes. Ligating the poly-nucleotide sequence into a gene construct, such as an expression vector, and transforming or transfecting into hosts, either eukaryotic (yeast, avian, insect or mammalian) or prokaryotic (bacterial) cells, are standard procedures.

A recombinant FAD-I nucleic acid can be produced by ligating the cloned gene, or a portion thereof, into a vector suitable for expression in either prokaryotic cells, eukaryotic cells, or both. Expression vehicles for production of a recombinant FAD-I polypeptides include plasmids and other vectors. For instance, suitable vectors for the expression of a FAD-I polypeptide include plasmids of the types: pBR322-derived plasmids, pEMBL-derived plasmids, pEX-derived plasmids, pBTac-derived plasmids and pUC-derived plasmids for expression in prokaryotic cells, such as E. coli.

A number of vectors exist for the expression of recombinant proteins in yeast. For instance, YEP24, YIP5, YEP51, YEP52, pYES2, and YRP17 are cloning and expression vehicles useful in the introduction of genetic constructs into S. cerevisiae (see, for example, Broach et al., (1983) in Experimental Manipulation of Gene Expression, ed. M. Inouye Academic Press, p. 83, incorporated by reference herein). These vectors can replicate in E. coli due the presence of the pBR322 ori, and in S. cerevisiae due to the replication determinant of the yeast 2 micron plasmid. In addition, drug resistance markers such as ampicillin can be used.

The preferred mammalian expression vectors contain both prokaryotic sequences to facilitate the propagation of the vector in bacteria, and one or more eukaryotic transcription units that are expressed in eukaryotic cells. The pcDNAI/amp, pcDNAI/neo, pRc/CMV, pSV2gpt, pSV2neo, pSV2-dhfr, pTk2, pRSVneo, pMSG, pSVT7, pko-neo and pHyg derived vectors are examples of mammalian expression vectors suitable for transfection of eukaryotic cells. Some of these vectors are modified with sequences from bacterial plasmids, such as pBR322, to facilitate replication and drug resistance selection in both prokaryotic and eukaryotic cells. Alternatively, derivatives of viruses such as the bovine papilloma virus (BPV-1), or Epstein-Barr virus (pHEBo, pREP-derived and p205) can be used for transient expression of proteins in eukaryotic cells. Examples of other viral (including retroviral) expression systems can be found below in the description of gene therapy delivery systems. The various methods employed in the preparation of the plasmids and transformation of host organisms are well known in the art. For other suitable expression systems for both prokaryotic and eukaryotic cells, as well as general recombinant procedures, see Molecular Cloning A Laboratory Manual, 2nd Ed., ed. by Sambrook, Fritsch and Maniatis (Cold Spring Harbor Laboratory Press, 1989) Chapters 16 and 17. In some instances, it may be desirable to express the recombinant FAD-I polypeptide by the use of a baculovirus expression system. Examples of such baculovirus expression systems include pVL-derived vectors (such as pVL1392, pVL1393 and pVL941), pAcUW-derived vectors (such as pAcUW1), and pBlueBac-derived vectors (such as the β-gal containing pBlueBac III).

It is well known in the art that a methionine at the N-terminal position can be enzymatically cleaved by the use of the enzyme methionine aminopeptidase (MAP). MAP has been cloned from E. coli (Ben-Bassat et al., (1987) J. Bacteriol. 169:751-757) and Salmonella typhimurium and its in vitro activity has been demonstrated on recombinant proteins (Miller et al., (1987) PNAS USA 84:2718-1722). Therefore, removal of an N-terminal methionine, if desired, can be achieved either in vivo by expressing such recombinant polypeptides in a host which produces MAP (e.g., E. coli or CM89 or S. cerevisiae), or in vitro by use of purified MAP (e.g., procedure of Miller et al.).

In another embodiment, a fusion gene coding for a purification leader sequence, such as a poly-(His)/enterokinase cleavage site sequence at the N-terminus of the desired portion of the recombinant protein, can allow purification of the expressed fusion protein by affinity chromatography using a $Ni^{2+}$ metal resin. The purification leader sequence can then be subsequently removed by treatment with enterokinase to provide the purified FAD-I polypeptide (e.g., see Hochuli et al., (1987) J. Chromatography 411:177; and Janknecht et al., PNAS USA 88:8972).

Techniques for malting fusion genes are well known. Essentially, the joining of various DNA fragments coding for different polypeptide sequences is performed in accordance with conventional techniques, employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed to generate a chimeric gene sequence (see, for example, Current Protocols in Molecular Biology, eds. Ausubel et al., John Wiley & Sons: 1992).

4. Defensin-stimulating Compositions

In certain aspects, the application provides compositions comprising a FAD-I and an excipient. Such compositions may be designed for delivery systemically or locally, and may be formulated for administration in any convenient way for use in human or veterinary medicine. In certain embodiments, the defensin-stimulating composition is formulated for local delivery to a particular epithelium, optionally a mucosal epithelium. For example, a composition may be formulated for delivery to the mouth, the eye, the skin, the vagina, the rectum, the intestines and the nose or other airways. In certain embodiments, the application provides methods for making a medicament comprising a FAD-I and an excipient for the administration by one of the above-described modes.

Thus, another aspect of the present invention provides compositions, optionally pharmaceutically acceptable compositions, comprising an amount, optionally a therapeutically-effective amount, of one or more of the compounds described above, formulated together with one or more excipients, including additives and/or diluents. As described in detail below, the compositions may be specially formulated for administration in solid or liquid form, including those adapted for the following: (1) systemic or local oral administration, for example, drenches (aqueous or non-aqueous solutions or suspensions), tablets, boluses, powders, granules, pastes for application to the tongue, toothpastes, mouthwashes, or films (e.g., the type of films used in Listerine PocketPaks®); (2) parenteral administration, for example, by subcutaneous, intramuscular or intravenous injection as, for example, a sterile solution or suspension; (3) topical application, for example, as a cream, ointment or spray applied to the skin; or (4) intravaginally or intrarectally, for example, as a pessary, cream or foam. However, in certain embodiments the subject FAD-I compounds may be simply dissolved or suspended in sterile water.

The phrase "therapeutically-effective amount" as used herein means that amount of a compound, material, or composition comprising a compound of the present invention which is effective for producing some desired therapeutic effect by increasing production of BD-2, BD-3, or both in at least a sub-population of cells in an animal.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "excipient" as used herein means a material, composition or vehicle, such as a liquid or solid filler, diluent, excipient, solvent or encapsulating material, optionally pharmaceutically-acceptable, involved in administering the subject FAD-I polypeptides. Each excipient should be compatible with the other ingredients of the formulation and not injurious to the subject. Some examples of materials which can serve as pharmaceutically-acceptable excipients include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

Compositions may also include excipients that are salts, preferably relatively non-toxic, inorganic and organic acid salts. These salts can be prepared in situ during the final isolation and purification of the compounds of the disclosure, or by separately reacting a purified compound with a suitable organic or inorganic acid, and isolating the salt thus formed. Representative salts include the chloride, hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, for example, Berge et al. (1977) "Pharmaceutical Salts", J. Pharm. Sci. 66:1-19). Other salts include those derived from inorganic acids such as hydrochloride, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isothionic, and the like.

In other cases, the compounds of the present invention may contain one or more acidic functional groups and, thus, are capable of forming pharmaceutically-acceptable salts with pharmaceutically-acceptable bases. The term "pharmaceutically-acceptable salts" in these instances refers to the relatively non-toxic, inorganic and organic base addition salts of compounds of the present invention. These salts can likewise be prepared in situ during the final isolation and purification of the compounds, or by separately reacting the purified compound in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like. (See, for example, Berge et al. supra).

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like: (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as tooth pastes or mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the FAD-I polypeptide.

Formulations of the present invention which are suitable for vaginal administration also include pessaries, tampons, creams, gels, pastes, foams or spray formulations containing such carriers as are known in the art to be appropriate.

Dosage forms for the topical or transdermal (systemic) or dermal (local) administration of a compound of this invention include powders, sprays, ointments, pastes, creams, lotions, gels, solutions, patches and inhalants. The active compound may be mixed under sterile conditions with a pharmaceutically-acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Ophthalmic formulations, eye ointments, powders, solutions and the like, are also contemplated as being within the scope of this invention.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissue.

When the compounds of the present invention are administered as pharmaceuticals, to humans and animals, they can be given per se or as a pharmaceutical composition containing, for example, 0.1 to 99.5% (more preferably, 0.5 to 90%) of active ingredient in combination with a pharmaceutically acceptable carrier.

The addition of the active compound of the invention to animal feed is preferably accomplished by preparing an appropriate feed premix containing the active compound in an effective amount and incorporating the premix into the complete ration.

Alternatively, an intermediate concentrate or feed supplement containing the active ingredient can be blended into the feed. The way in which such feed premixes and complete rations can be prepared and administered are described in reference books (such as "Applied Animal Nutrition". W.H. Freedman and CO., San Francisco, U.S.A., 1969 or "Livestock Feeds and Feeding" O and B books. Corvallis, Oreg., U.S.A., 1977).

FAD-I may be incorporated into contraceptives, such as condoms, female condoms, spermicidal ointment, contraceptive sponges and the like.

In yet another embodiment, the FAD-I protein can be administered as part of a combinatorial therapy with other agents. For example, the combinatorial therapy can include a FAD-I protein with at least one antibacterial, antiviral or antifungal agent. A combinatorial therapy may include a FAD-I protein and a chemotherapeutic agent, such as cytosine, arabinoside, 5-fluorouracil, hydroxyurea, and methotrexate.

5. Methods for Using Defensin-Stimulating Compositions

In certain embodiments, the application provides methods for treating a variety of diseases by administering a defensin-inducing composition comprising a FAD-I. Examples of diseases to be treated include infectious diseases of the various epithelial tissues, including conjunctivitis, gingivitis, tooth decay, sinusitis, urinary tract infections, gastroenteritis and dermatitis, any of which may be bacterial, fungal or viral in origin. Diseases to be treated include systemic infectious diseases as well. In certain embodiments, compositions comprising an FAD-I may be used to treat infections that are resistant to one or more other antimicrobial agents, such as vancomycin resistant *Enterococcus* or methicillin resistant *Staphylococcus aureus*, penicillin or cephalosporin resistant *Pneumococcus*, multi-drug resistant *Pseudomonas*, to name only a few. Cancers may also be treated using compositions disclosed herein, including squamous cell carcinomas, such as oral squamous cell carcinomas, and other tumor types. In addition, compositions disclosed herein may be used to bolster the immune system of immunocompromised patients.

In certain aspects the application provides methods for stimulating BD-2 production, BD-3 production, or both, comprising contacting a cell with a composition comprising a FAD-I. In certain preferred embodiments, the cell is an epithelial cell, optionally an epithelial cell located in a vertebrate such as a human. In certain exemplary embodiments, the epithelial cell is an oral epithelial cell, a corneal epithelial cell or a keratinocyte. In certain embodiments, the epithelial cell is a mucosal epithelial cell.

BD-2 polypeptides are known promote maturation and/or production of immune cells, such as dendritic cells. Biragyn et al. 2002 Science 298:1025-29. These cells are important in many aspects of immunity, including recognition and destruction of a wide variety of cancers. Accordingly, compositions disclosed herein are suitable for treatment of cancers, as. well for bolstering the immune response of immunocompromised patients, such as, for example, patients that have received irradiation therapy or patients that suffer from a immunodeficiency syndrome, such as that caused by HIV.

BD-2s and BD-3s exhibit broad-spectrum antimicrobial activity and are active against a range of bacteria, including gram negative and gram positive bacteria. Accordingly, FAD-I may be used to treat systemic and local infections of any of these bacteria. For example, FAD-I may be used against bacteria that are responsible for periodontal disease, such *Porphyromonas gingivalis*.

BD-2s and BD-3s are also active against a range of pathogenic fungi. Garcia et al., 2001 Cell Tissue Res. 306(2):257-64. Accordingly, FAD-I may be used to treat systemic and local fungal infections. For example, FAD-I may be used to treat *Candida albicans* infections. *C. albicans* is the causative agent for many yeast infections in women, as well as for monocutaneous fungal disease in HIV patients.

BD-2s and BD-3s are active against viral agents, and particularly enveloped viruses, such as many retroviruses and RNA viruses, including lentiviruses such as HIV and SIV.

Unlike most antimicrobial agents, resistance to beta-defensins is rare in pathogenic organisms. Accordingly, FAD-I may be used in situations where use of a traditional antimicrobial agent would be ill-advised because of the risk of resistance development. For example, FAD-I may be administered to patients that are at risk for an infection, as in the case of immunocompromised patients, as well as people who expect to encounter infectious agents. 6. Methods for Identifying Defensin-Stimulating Compositions In certain aspects, the application provides methods of screening for agents that induce an innate immune response in a human comprising providing a cellular extract of a commensal microorganism and determining a change in the innate immune response of an organism or cell. In certain embodiments, the commensal microorganism is a bacterium resistant against BD-2, BD-3, or both. In certain embodiments, the change in the innate immune response is stimulation of BD-2 expression, BD-3 expression, or both in a cell.

Amongst the many bacteria that have evolved to reside on our mucosal surfaces, some have mutualistic relationships with the human host; a continuum between commensalism and symbiosis. Commensal bacteria are generally regarded as beneficial to the host by displacing pathogens from a microbial niche or by secreting antimicrobial substances. Recent data suggest that commensals also provide protection by chronically stimulating epithelial surfaces to express antimicrobial peptides (APs) at levels that kill opportunistic/pathogenic organisms. As described herein, certain commensal bacteria, such as *F. nucleatum* are resistant to elements of the innate immune system and induce expression of same. While not wishing to be bound to mechanisms, it is hypothesized that this is a means of competition against other non-resistant bacteria. Accordingly, commensal bacteria will be a rich source of agents that modulate the innate immune system, and commensals that are resistant to elements of the innate immune system will be particularly good candidates.

7. Effective Dose

Toxicity and therapeutic efficacy of such compounds can be determined by standard pharmaceutical procedures in cell cultures or experimental animals, e.g., for determining The Ld50 (The Dose Lethal To 50% Of The Population) And The Ed50 (the dose therapeutically effective in 50% of the population). The dose ratio between toxic and therapeutic effects is the therapeutic index and it can be expressed as the ratio LD50/ED50. Compounds which exhibit large therapeutic induces are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

The invention now being generally described, it will be more readily understood by reference to the following examples, which are included merely for purposes of illustration of certain aspects and embodiments of the present invention, and are not intended to limit the invention.

The practice of the present invention may employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, *Molecular Cloning A Laboratory Manual,* 2nd Ed., ed. by Sambrook, Fritsch and Maniatis (Cold Spring Harbor Laboratory Press: 1989); *DNA Cloning,* Volumes I and II (D. N. Glover ed., 1985); *Oligonucleotide Synthesis* (M. J. Gait ed., 1984); Mullis et al. U.S. Pat. No. 4,683,195; *Nucleic Acid Hybridization* (B. D. Hames & S. J. Higgins eds. 1984); *Transcription And Translation* (B. D. Hames & S. J. Higgins eds. 1984); *Culture Of Animal Cells* (R. I. Freshney, Alan R. Liss, Inc., 1987); *Immobilized Cells And Enzymes* (IRL Press, 1986); B. Perbal, *A Practical Guide To Molecular Cloning* (1984); the treatise, *Methods In Enzymology* (Academic Press, Inc., N.Y.); *Gene Transfer Vectors For Mammalian Cells* (J. H. Miller and M. P. Calos eds., 1987, Cold Spring Harbor Laboratory); *Methods In Enzymology,* Vols. 154 and 155 (Wu et al. eds.), *Immunochemical Methods In Cell And Molecular Biology* (Mayer and Walker, eds., Academic Press, London, 1987); *Handbook Of Experimental Immunology,* Volumes I-IV (D. M. Weir and C. C. Blackwell, eds., 1986); *Manipulating the Mouse Embryo,* (Cold Spring Harbor Laboratory Press, Cold Spring Harbor, N.Y., 1986).

EXEMPLIFICATION

The invention now being generally described, it will be more readily understood by reference to the following examples, which are included merely for purposes of illustration of certain aspects and embodiments of the present invention, and are not intended to limit the invention.

We have identified in *F. nucleatum,* a heat stable, cell surface associated factor that induces hBD-2, hBD-3, or both in NHOECs, and consequently protects them from *P. gingivalis* invasion. We refer to this agent as FAD-I for *Fusobacterium* associated defensin inducer. KB cells from an oral cell line that originated from a human oral squamous cell carcinoma (ATCC CCL-17), did not express hBD-2 after FAD-I challenge, and were not protected from *P. gingivalis* invasion. A 40 kDa cell wall associated component bound NHOEC surface proteins but failed to bind an equivalent fraction from KB cells. Organic extraction of the cell wall fraction of *F. nucleatum* generated a water soluble top layer that induces hBD-2. Proteinase K digestion of the top layer abolished both the hBD-2 inducibility and the 40 kDa component. Further biochemical analyses, along with bioactivity studies of FAD-I identified FAD-I as the polypeptide of SEQ ID NO.:1.

The top layer fraction increased hBD-2 expression in NHOECs with minimal induction of IL-8. This correlates with in vivo findings showing that while hBD-2 is expressed only in the presence of infection or inflammation in skin, trachea and gut epithelium, in oral tissues it is expressed in normal uninflamed conditions. Our results also showed that hBD-3 expression in normal human skin keratinocytes was induced by *F. nucleatum* cell wall. Our results, therefore demonstrate that *F. nucleatum* has the ability to activate epithelial cells in a discrete and limited manner; i.e., induction of hBD-2 without IL-8. Further, NF-kB, is neither necessary nor sufficient for *F. nucleatum* induction of hBD-2. Instead, MAP kinase pathways, p38 and JNK are utilized. These results are consistent with the hypothesis that *F. nucleatum* has evolved to generate a heightened state of readiness of the epithelium it inhabits without fully unleashing other innate immune responses. This does not mean that *F. nucleatum* doesn't have the ability to upregulate IL-8, nor does it mean that this organism maintains the same symbiotic relationship with the host in all body sites. Other components of *F. nucleatum,* such as LPS, can activate expression of IL-8 in NHOECs, and this organism may use its inherent resistance to defensins as a virulence strategy in its ability to invade epithelial cells, and possibly in association with systemic complications such as amniotic fluid infections that lead to preterm births.

Example 1

*Fusobacterium* Associated Defensin Inducer

Untreated cell wall supernatant from *F. nucleatum* (ATCC 25586) was charged onto a C4 HPLC column and fractions were eluted with an acetonitrile gradient and tested for hBD-2 mRNA induction of normal human oral epithelial cell (NHOEC) monolayers by RT-PCR. The shoulder that eluted at 47-50% acetonitrile, and is designated with an asterisk/arrow in FIG. 1A, induced hBD-2 mRNA (FIG. 1B; lane 3).

Figure 2:
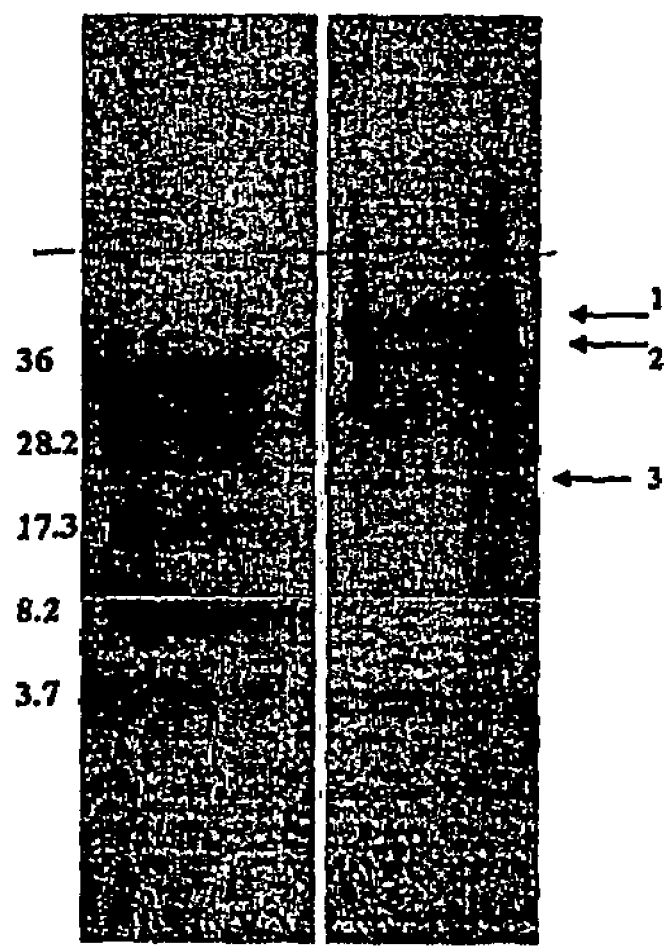
FIG. 2. SDS-PAGE of hBD-2 inducing fraction. Asterisks show 3 bands that were excised for trypsin digest and amino acid sequencing. Band 1 was identified as FomA, pI 9.2. Band 2, was also identified as FomA. Band 3 contained 2 proteins identified as, 12.5 kDa (pI 4.3) (NP_602592; Accession no. 19705097), and 14.8 kDa (pI 5.3)(Accession no. 19704859).
Figure 3:
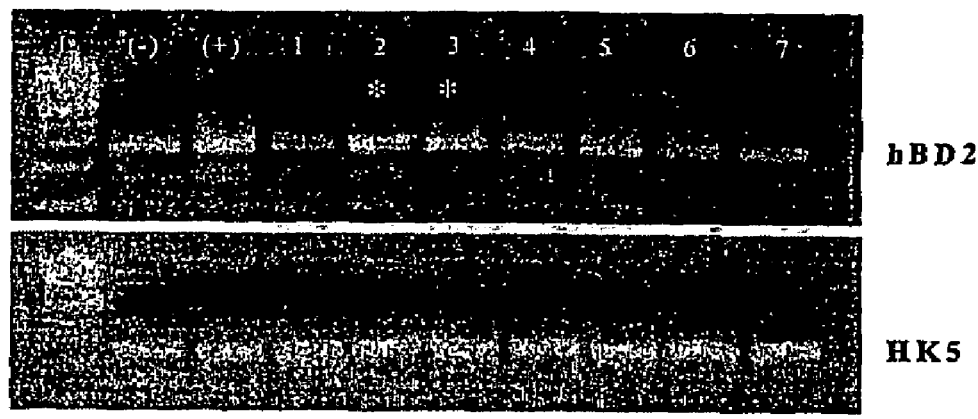
FIG. 3. RT-PCR of IEF focused fractions of soluble *F. nucleatum* cell wall that induce hBD-2 in NHOECs. Soluble *F. nucleatum* cell wall was isoelectrically focused in a pI gradient of 3 to 10 using a ninipreparative Rotofor Cell (Bio-Rad). Samples were concentrated using Centricon YM-3 filters (Amicon) to remove ampholytes, and NHOEC monolayers were challenged with respective fractions, followed by RT-PCR analysis. Note that predominant hBD-2 mRNA induction was identified in lanes 2 and 3 (asterisks). All other lanes showed no hBD-2 mRNA induction. The mean pH tested per lane: 1, pH 3.0; 2, pH 3.8; 3, pH 5.0; 4, pH 6.3; 5, pH 7.3; 6, pH 8.3; 7, pH 9.5. (−), no challenge; (+), PMA; HK5, human keratin 5.
Figure 4:
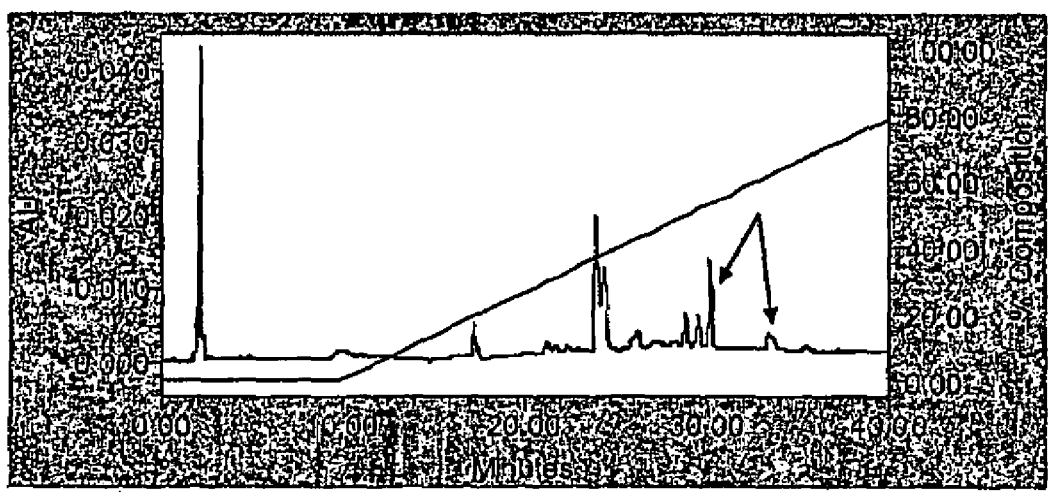
FIG. 4. HPLC chromatogram of Rotofor Cell fraction pI 3.8. A pI 3.8 sample from the Rotofor Cell that was found to induce hBD-2 mRNA in NHOECs, was charged onto a C4 HPLC column and eluted at various time points in an acetonitrile gradient (blue). Arrows point to candidate peaks in the 30-35 min elution fraction that was found to induce hBD-2 without inducing IL-8 (see FIG. 5 below).
Figure 5:
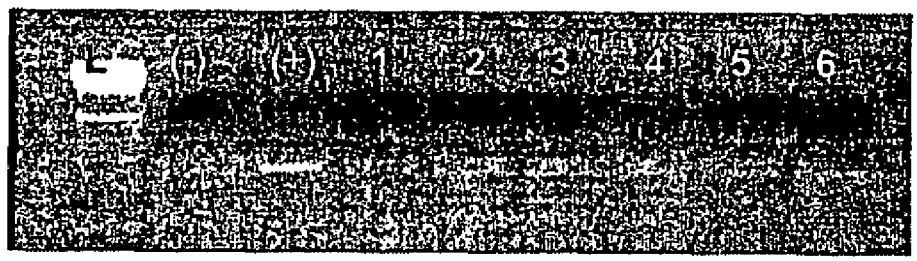
FIG. 5. RT-PCR analysis of hBD-2 mRNA induction in NHOECs after challenge with HPLC fractions of Rotofor Cell samples, pI 3.8 and pI 5.0. IEF isolated fractions that were previously shown to induce hBD-2 mRNA in NHOECs, pI 3.8 and 5.0, were subjected to HPLC fractionation in an acetonitrile gradient followed by incubation with NHOEC monolayers and RT-PCR analysis, respectively. Note that lane 4, representing an HPLC fraction from the pH 3.8 sample, that eluted at 30-35 minutes and at an acetonitrile concentration of 52-66%, shows hBD-2 mRNA induction, with apparent inhibition of IL-8 mRNA. Lane 6, from an HPLC fraction of pH 5.0, that eluted at 30-35 minutes and at an acetonitrile concentration of 52-66%, also induced hBD-2 mRNA to a lesser degree, but without inhibiting IL-8. L, m.w. ladder; (−), no challenge; (+), PMA; 1, HPLC fraction of pH 3.8, 0-10 min elution; 2, HPLC fraction of pI 3.8, 20-25 min elution; 3, HPLC fraction of pI 3.8, 25-30 min elution; 4, HPLC fraction of pI 3.8, 30-35 min elution; 5, HPLC fraction of pI 5.0, 25-30 min elution; 6, HPLC fraction of pI 5.0, 30-35 min elution.
Figure 5:
Figure 5:
Figure 6:
FIG. 6. RT-PCR analysis of hBD-2 mRNA induction in NHOECs after challenge with HPLC fractions of Rotofor Cell samples, with mean pIs of 1.5, 6.3, 7.3, 8.3 and 9.5. IEF isolated samples with a mean pI of 1.5, 6.3, 7.3, 8.3, and 9.5 were subjected to HPLC fractionation in an acetonitrile gradient followed by incubation with NHOEC monolayers and RT-PCR analysis, respectively. No fraction induced hBD-2 transcript. L, m.w. ladder; (−), no challenge; (+), PMA; 1, HPLC fraction of pI 1.5, 20-25 min elution; 2, HPLC fraction of pI 1.5, 25-30 min elution; 3, HPLC fraction of pI 6.3, 20-25 min elution; 4, HPLC fraction of pI 6.3, 25-30 min elution; 5, HPLC fraction of pI 6.3, 30-35 min elution; 6, HPLC fraction of pI 7.3, 20-25 min elution; 7, HPLC fraction of pI 7.3, 25-30 min elution; 8, HPLC fraction of pI 7.3, 30-35 min elution, 9, HPLC fraction of pI 8.3, 20-25 min elution; 10, HPLC fraction of pI 8.3, 25-30 min elution; 11, HPLC fraction of pI 8.3, 30-35 min elution; 12, HPLC fraction of pI 9.5, 20-25 min elution; 13, HPLC fraction of pI 9.5, 25-30 min elution; 14, HPLC fraction of pI 9.5, 30-35 min elution.
Figure 7:
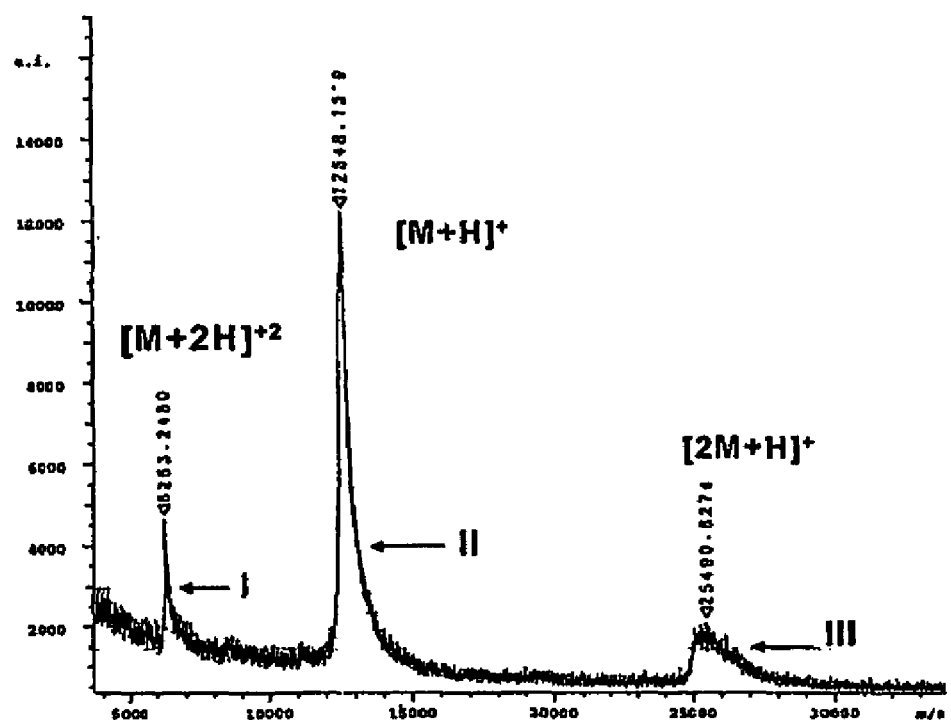
FIG. 7. MALDI-MS of HPLC active fraction. The HPLC fraction from the mean pI 3.8 sample that was bioactive (FIG. 5), was analyzed by MALDI-MS. The solvent used was a 1:1 mixture of acetonitrile and water with 0.1% TFA. The sample was mixed 1:1 with the matrix sinapinic acid and 1 μl was spotted onto the target. The samples were run on a Bucher Reflex II MALDI TOF instrument operating in linear and positive ion modes. Based on peak width, the three fragments seen are derived from the same protein. The 12.5 kDa peak (designated as II) is a singly charged ion (M+H+). The 6.25 kDa peak (designated as I) is a doubly charged ion (M+2H+). The 25.5 kDa peak (designated as III) is a proton bound dimer (2M+H+). Accordingly the active polypeptide is the 12.5 kDa polypeptide (pI 4.3) (NP_602592; Accession no. 19705097).

An aliquot of the active fraction was subjected to SDS-PAGE electrophoresis, and three bands were excised for trypsin digest and amino acid sequencing (FIG. 2, asterisks). The data was analyzed by using collision induced dissociation (CID) spectra to search the NCBI non-redundant data base with the search program TurboSequest. The major band was identified as FomA, the major outer membrane protein of *F. nucleatum* with a pI 9.2 (31 peptides covering 76% of the protein sequence). The second band (FIG. 2, arrow #2) was also identified as FomA. Two proteins were identified from the third band (FIG. 2, light band designated by arrow #3). One was 12.5 kDa, pI 4.3 (5 peptides covering 39% of the protein sequence) and the second was 14.8 kDa, pI 5.3, (3 peptides covering 33% of the protein sequence). Using the differences in pI of these three identified proteins, isoelectric focusing was performed on the sonicated cell wall supernatant in the range of 3 to 10. Two active fractions in the range of 3.8 to 5.0 mean pI were identified that induced hBD-2 (FIG. 3; lanes 2,3). All other fractions, including those in the pI range for FomA, did not induce hBD-2 above baseline (FIG. 3; lanes 6, 7). The pI 3.8 and 5.0 samples from the Rotofor Cell were charged onto a C4 HPLC column and eluted at various time points in an acetonitrile gradient, respectively. FIG. 4, shows the chromatogram of the pI 3.8 sample. Interestingly, a fraction from this sample eluting in the range of 52-66% acetonitrile and at 30-35 minutes, induced hBD-2 mRNA above baseline (FIG. 5; Lane 4). The chromatogram identified two peaks (FIG. 4, arrows). A fraction from the pI 5.0 sample, with similar acetonitrile concentration and elution time coordinates, also induced hBD-2 MnRNA, albeit to a lesser degree (FIG. 5, lane 6). However, only the fraction from the pI 3.8 sample induced hBD-2 mRNA without concomitant induction of IL-8 (FIG. 5, compare lanes 4 and 6 for hBD-2 and IL-8). In fact, the fraction in lane 4 appeared to inhibit IL-8 mRNA when compared to baseline. Rotofor Cell samples of the other mean pI ranges were also fractionated by HPLC as described for the pH 3.8 and 5.0 samples, and tested on NHOEC monolayers for hBD-2 mRNA induction. These fractions did not induce the hBD-2 transcript (FIG. 6). Linear MALDI-MS spectra of the HPLC active fraction obtained either from organically treated or soluble cell wall, contain the 12.5 kDa singly charged ion, the 6.25 doubly charged ion and the proton bound dimer at 25.5 kDa (FIG. 7). Based on mass spectrometry analysis (peak width), the three fragments derive from the same source.

In summary, we have now confirmed, through repeated experiments and multiple MALDI-MS and CID analyses, that the hBD-2 inducing BPLC fraction from soluble *F. nucleatum* cell wall, elutes at 30-35 minutes and contains a hydrophobic 12.5 kDa peptide that is in the pH range of 3.8-4.2. This is the polypeptide of SEQ ID NO.:1.

Example 2

Identifying other Human Epithelial Cell Types that Express hBD-2 mRNA upon *F. nucleatum* Challenge We challenged human corneal epithelial cells and skin keratinocytes with *F. nucleatum* cell wall (under identical conditions described in Preliminary Studies for NHOEC's) followed by RT-PCR analysis.

Figure 8:
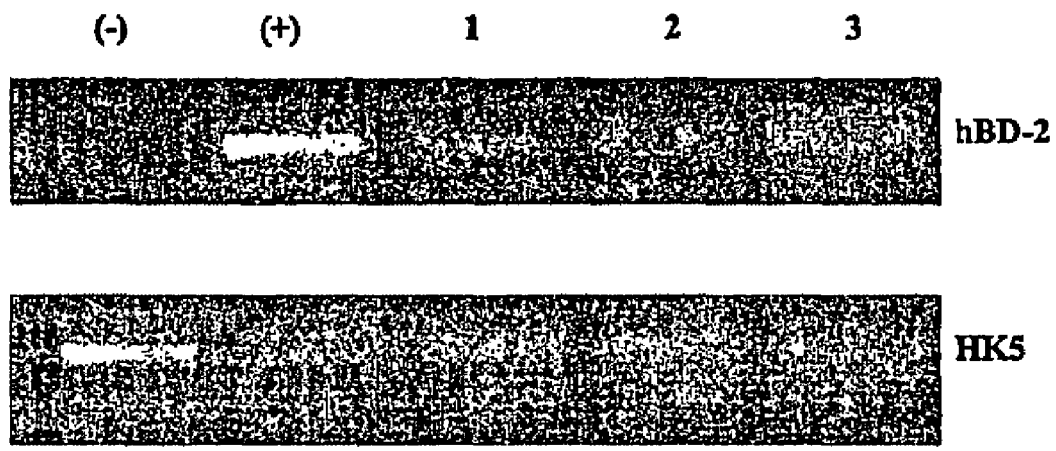
FIG. 8. *F. nucleatum* induces hBD-2 mRNA in human corneal epithelial cells (HCE-T). HCE-T monolayers were grown as described in Maldano and Furcht, 1995 [2] and challenged with increasing concentrations of an *F. nucleatum* cell wall fraction (Fn), 18 hr, followed by RT-PCR analysis. Note a dose dependent increase in hBD-2 transcript. (−)=no challenge; (+)=PMA, positive control; Lane 1, 0.1 μg/ml Fn; Lane 2, 1 μg/ml Fn; Lane 3, 5 μg/ml Fn.

We obtained SV40 transformed human corneal epithelial cells (HCE-T) and grew them in monolayers as described by Maldonado and Furcht, 1995. HCE-T cells have been shown to express properties similar to normal corneal epithelial cells and don't produce free viral particles, nor have been shown to revert to a viral producing cell line. Upon challenge with increasing concentrations of the *F. nucleatum* cell wall fraction, there was a concomitant increase in hBD-2 transcript expression (FIG. 8).

Figure 9:
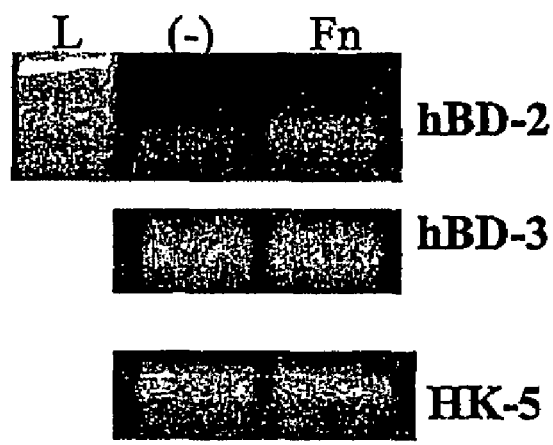
FIG. 9. *F. nucleatum* induces beta defensins in human skin keratinocytes. Normal human skin keratinocytes were obtained from a kceratome biopsy, isolated, cultured as described in Chen et al, 2001, and challenged with *F. nucleatum* cell wall (5 μg/ml) overnight. RT-PCR analysis revealed induction of both hBD-2 and hBD-3 mRNA. PMA was not included in this experiment. (−)=negative control.

Primary normal human skin keratinocyes (NHSKs) were obtained from a keratome biopsy through the Department of Dermatology (University Hospitals, Cleveland, Ohio). They were isolated and cultured as described previously, followed by challenge with *F. nucleatum* cell wall. RT-PCR analysis revealed that both hBD-2 and -3 mRNA were induced (FIG. 9).

Example 3

Generation of a Transient Reporter Gene Construct System in OKF6/Tert Cells to Detect Induction of hBD-2

We have conducted extensive studies comparing beta defensin regulation by *F. nucleatum*, *P. gingivalis*, A. actinomycetemcomitans, and different isolates of *C. albicans* in NHOEC's and the immortalized human oral cell line OKF/Tert cells (terts). We have concluded that in all our recorded cases, terts behave like NHOEC's. We therefore decided to use terts as our cell source for the generation of a transient reporter gene construct system.

Figure 10:
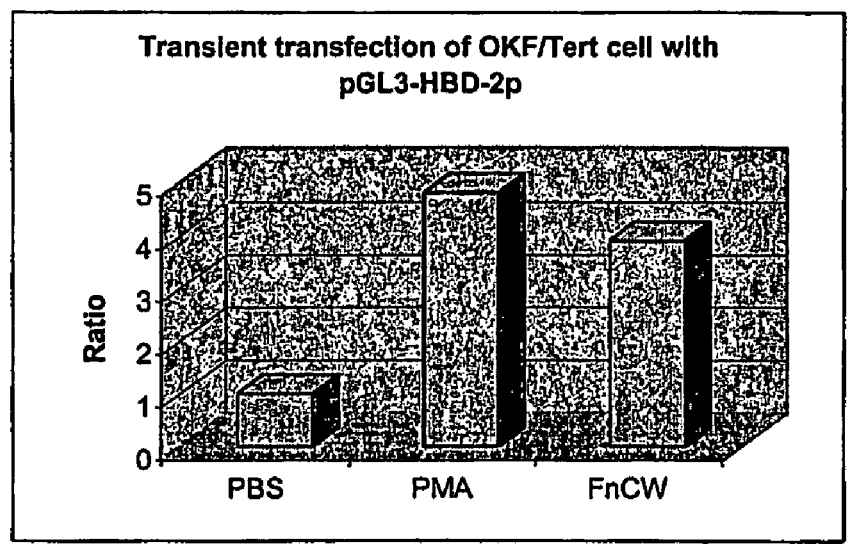
FIG. 10. Transient reporter gene construct in OKF6/Tert cells. Tert cells were transfected with pGL3-HBD-2, using LipofectAMINE reagent (Invitrogen, Carlsbad, Calif.), following the manufacturer's instruction, and the luciferase reporter assay (Promega) was used as the readout. When the PBS challenged cell result was arbitrarily set to a level of 1 (designated as "Ratio" in the figure), a four fold increase in expression was shown with the *F. nucleatum* cell wall challenged cells.

Tert cells were transfected with pGL3-HBD-2p (gift from Jürgen Harder and Jens Schröder, Kiel University, Germany). This construct involved PCR amplifying the hBD-2 promoter (1284 bp upstream of the reading frame) and using Hind III and Xho I to ligate the promoter to the firefly luciferase gene in the pGL3 vector. Transfection was conducted with LipofectAMINE reagent (Invitrogen, Carlsbad, Calif.), following the manufacturer's instruction. Briefly, cells were loaded into 24 well plates and grown to near confluence. Serum free DMEM was used as the transfection medium. The transfection cocktail was prepared in the following way (per well): plasmid DNA (1 μg) was added to 25 μl DMEM, along with 4 μl PLUS reagent mix, followed by incubation at room temperature for 15 min. LipofectAMINE reagent (1 μl) was added to 25 μl DMEM. The plasmid mix and the LipofectAMINE mix were combined and incubated at room temperature for 15 min. After removal of culture medium, the combined DNA-PLUS-LipofectAMINE mixture was added to each well along with 0.2 ml DMEM, followed by incubation at 37C, 5% CO2, 3 hr. The transfection medium was then replaced with fresh DMEM, and incubated for an additional 24 hr. Cells were then challenged with either PBS, PMA, or *F. nucleatum* cell wall (10 μg/ml). We used the luciferase reporter assay system (Promega, Madison, Wis.) to detect the expression of luciferase. FIG. 10 is representative of the results obtained and show that there is a 4 fold increase above baseline in luciferase expression in cells challenged with *F. nucleatum* cell wall.

Example 4

Figure 11:
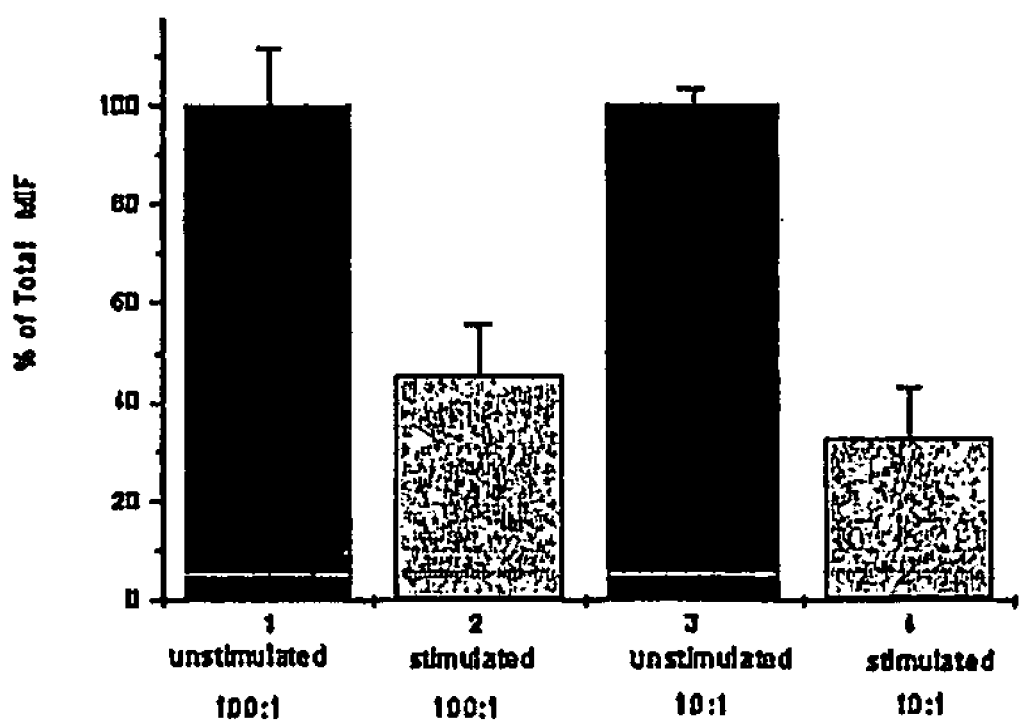
FIG. 11. *F. nucleatum* stimulation of normal human oral epithelial cells (NHOECs) confers protection against *P. gingivalis* invasion. NHOEC semi-confluent (80%) monolayers were challenged with *F. nucleatum* cell wall fraction (10 □g/ml) for approximately 18 hrs. *P. gingivalis* was then added at an MOI of 10:1 or 100:1, 90 min, 37° C., 5% CO2. After 1 hour incubation with gentamycin and metronidazole, cells were harvested and subjected to flow cytometric analysis. Results revealed a 54.3% and 67.2% reduction in *P. gingivalis* invasion for the 100:1 and 10:1 MOI's respectively, when compared to non *F. nucleatum* stimulated NHOECs. Results represent the mean±SD from three separate experiments using 3 different NHOEC donor cells. P<0.05 using paired student's T test. MFI, mean fluorescence intensity.

*F. nucleatum* Induction of Beta Defensins Protects NHOECs from Bacterial Invasion We compared hBD-2 induced normal human oral epithelial cells (NHOECs), after *F. nucleatum* challenge, with uninduced, quiescent NHOECs to determine protection against *P. gingivalis* invasion. Semi-confluent monolayers were challenged with *F. nucleatum* overnight, to induce hBD-2 expression. Unstimulated and *F. nucleatum* stimulated NHOEC monolayers were challenged with syto 62 labeled *P. gingivalis* at an MOI of 10:1 and 100:1. After a 90 minute incubation, followed by one hour antibiotic treatment to kill all extracellular bacteria (64, 65), cells were analyzed by flow cytometry. The *F. nucleatum* prestimulated cells were more than 50% protected when compared to the unstimulated cultures at an MOI of 100:1, and more than 67% protected at an MOI of 10:1 (FIG. 11).

These bioassays demonstrate the efficacy of protection elicited from physiologically relevant concentrations of cell associated hBD-2.

Figure 12:
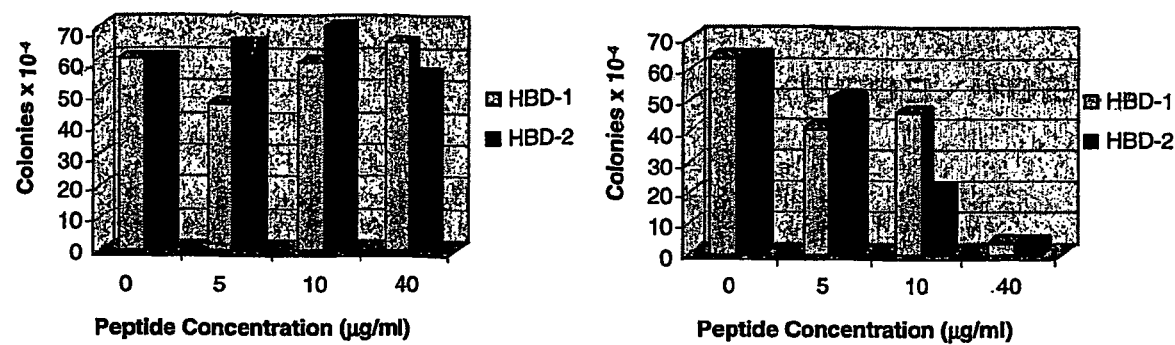
FIG. 12. Comparison of *F. nucleatum* and *P. gingivalis* resistance to recombinant hBD-1 and hBD-2. Recombinant hBD-1 and hBD-2 were generated using a baculovirus expression system with Sf21 insect cells (see appendix 6). Bacteria were incubated with either recombinant hBD-1 or -2, anaerobically, 3 hr, followed by serial dilutions and plating on sheep red blood agar plates. Analyses of the in vitro antimicrobial properties of recombinant hBD-1 and hBD-2 against *F. nucleatum* and *P. gingivalis* revealed that while *P. gingivalis* was ildled by both peptides at low micromolar concentrations, *F. nucleatum* was not.

*F. nucleatum* is resistant to recombinant hBD-1 and -2. After generating recombinant forms of hBD-1 and hBD-2, using a baculovirus expression system with Sf21 insect cells, we found that *F. nucleatum* was resistant to these agents, while *P. gingivalis* was sensitive to them in low micromolar concentrations (10 μg/ml hBD-1=2.55 μM; 10 μg/ml hBD-2=2.31 μM) (FIG. 12).

INCORPORATION BY REFERENCE

All publications and patents mentioned herein are hereby incorporated by reference in their entirety as if each individual publication or patent was specifically and individually indicated to be incorporated by reference. In case of conflict, the present application, including any definitions herein, will control.

1. Chen, G., et al., Basal keratinocytes from uninvolved psoriatic skin exhibit accelerated spreading and focal adhesion kinase responsiveness to fibronectin. Journal of Investigative Dermatology, 2001. 117: p. 1538-1545.
2. Maldonado, B. A. and L. T. Furcht, Epidermal growth factor stimulates integrin-mediated cell migration of cultured human corneal epithelial cells on fibronectin and arginine-glycine-aspartic acid peptide. Investigative Ophthalmology & Visual Science, 1995. 36(10): p. 2120-6.
3. Dickson, M. A., et al., Human keratinocytes that express hTERT and also bypass a p16(INK4a)-enforced mechanism that limits life span become immortal yet retain normal growth and differentiation characteristics. Mol Cell Biol, 2000. 20(4): p. 1436-47.
4. Araki-Sasaki, K., et al., An SV40-immortalized human corneal epithelial cell line and its characterization. Invest Ophthalmol Vis Sci, 1995. 36(3): p. 614-21.
5. Krisanaprakornkit, S., J. R. Kimball, and B. A. Dale, Regulation of human beta-defensin-2 in gingival epithelial cells: the involvement of mitogen-activated protein kinase pathways, but not the NF-kappaB transcription factor family. Journal of Immunology, 2002. 168(1): p. 316-24.
6. Ortega, M. R, T. Ganz, and S. M. Milner, Human beta defensin is absent in burn blister fluid. Burns, 2000. 26(8): p. 724-6.
7. Garcia J R, Jaumann F, Schulz S, Krause A, Rodriguez-Jimenez J, Forssmann U, Adermann K, Kluver E, Vogelmeier C, Becker D, Hedrich R, Forssmann W G, Bals R., Identification of a novel, multifunctional beta-defensin (human beta-defensin 3) with specific antimicrobial activity. Its interaction with plasma membranes of *Xenopus* oocytes and the induction of macrophage chemoattraction. Cell Tissue Res., 2001. 306(2):257-64.
8. Kapatral, V., Anderson, I., Ivanova, N., Reznik, G., Los, T., Lykidis, A., Bhattacharyya, A., Bartman, A., Gardner, W., Grechkin, G., Zhu, L., Vasieva, O., Chu, L., Kogan, Y., Chaga, O., Goltsman, E., Bernal, A., Larsen, N., D'Souza, M., Walunas, T., Pusch, G., Haselkorn, R., Fonstein, M., Kyrpides, N. and Overbeek, R., Genome sequence and analysis of the oral bacterium *Fusobacterium nucleatum* strain ATCC 25586. J. Bacteriol., 2002. 184 (7), 2005-2018

Equivalents

While specific embodiments of the subject invention have been discussed, the above specification is illustrative and not restrictive. Many variations of the invention will become apparent to those skilled in the art upon review of this specification and the claims below. The full scope of the invention should be determined by reference to the claims, along with their full scope of equivalents, and the specification, along with such variations.

I claim:

1. A defensin-stimulating composition, comprising an isolated polypeptide comprising SEQ. ID. NO. 1, and an excipient.

2. The defensin-stimulating composition of claim 1, wherein the polypeptide is a fusion protein additionally comprising an amino acid sequence heterologous to the amino acid sequence of SEQ ID NO.: 1.

3. The defensin-stimulating composition of claim 1, further comprising an antimicrobial agent.

4. The defensin-stimulating composition of claim 1, further comprising an antifungal agent.

5. The defensin-stimulating composition of claim 1 wherein the composition stimulates defensin production in an epithelial cell.

6. The defensin-stimulating composition of claim 1, wherein the composition stimulates defensin production in the mouth.

7. The defensin-stimulating composition of claim 6, wherein the composition is a mouth wash, toothpaste, or film.

8. The defensin-stimulating composition of claim 1, wherein the composition stimulates defensin production in the cornea.

9. The defensin-stimulating composition of claim 5, wherein the composition is an eye drop or eye cream.

10. The defensin-stimulating composition of claim 1, wherein the composition stimulates defensin production in the skin.

11. The defensin-stimulating composition of claim 10, wherein the composition is a skin cream or skin lotion.

* * * * *

UNITED STATES PATENT AND TRADEMARK OFFICE
CERTIFICATE OF CORRECTION

| | | |
|---|---|---|
| PATENT NO. | : 7,655,242 B2 | Page 1 of 1 |
| APPLICATION NO. | : 10/538811 | |
| DATED | : February 2, 2010 | |
| INVENTOR(S) | : Aaron Weinberg | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 967 days.

Signed and Sealed this

Twenty-third Day of November, 2010

David J. Kappos
*Director of the United States Patent and Trademark Office*